(12) United States Patent  
Surkov

(10) Patent No.: US 7,846,939 B2  
(45) Date of Patent: Dec. 7, 2010

(54) SALTS AND MIXTURE OF 9-OXOACRIDINE-10-ACETIC ACID WITH 1-ALKYLAMINO-1-DESOXY-POLYOLS, PHARMACEUTICAL COMPOSITIONS CONTAINING SAID AGENTS AND TREATMENT METHODS

(75) Inventor: Kirill Gennadievich Surkov, Saint Petersburg (RU)

(73) Assignee: EPhaG AS, Tallinn (EE)

( * ) Notice: Subject to any disclaimer, the term of this patent is extended or adjusted under 35 U.S.C. 154(b) by 66 days.

(21) Appl. No.: 12/094,479

(22) PCT Filed: Nov. 17, 2006

(86) PCT No.: PCT/RU2006/000614

§ 371 (c)(1),  
(2), (4) Date: Nov. 25, 2008

(87) PCT Pub. No.: WO2007/058568

PCT Pub. Date: May 24, 2007

(65) Prior Publication Data

US 2010/0144780 A1    Jun. 10, 2010

(30) Foreign Application Priority Data

Nov. 21, 2005    (RU)    ................................ 2005136819

(51) Int. Cl.  
    *A61K 31/44*      (2006.01)  
(52) U.S. Cl. ........................................ 514/290  
(58) Field of Classification Search ................. 514/290  
See application file for complete search history.

(56) References Cited

FOREIGN PATENT DOCUMENTS

RU     2 135 474 C1    8/1999

*Primary Examiner*—Raymond J Henley, III  
(74) *Attorney, Agent, or Firm*—Frommer Lawrence & Haug LLP; Ronald R. Santucci

(57) ABSTRACT

The invention relates to salts of 1-alkylamino-1-deoxypolyols and 9-oxoacridine-10-acetic acid of the general formula (I):

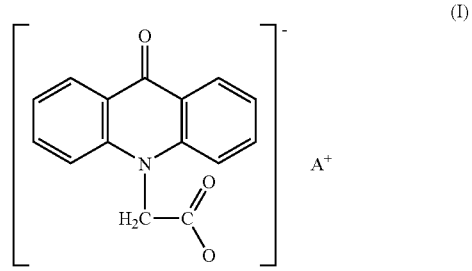

wherein $A^+$ is (II)

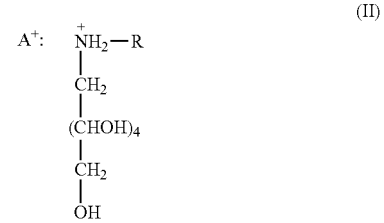

wherein R is selected from the group consisting of ethyl, propyl, butyl, medicinal preparations comprising as an active ingredient salts of formula (I) and/or a mixture of said salt of formula (I) or 9-oxoacridine-10-acetic acid of the formula:

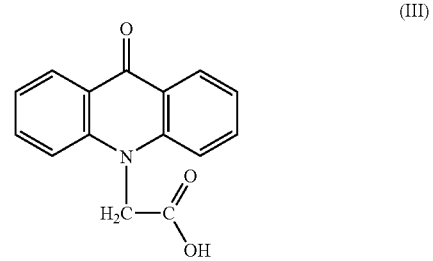

and one or more 1-alkylamino-1-deoxypolyols of the general formula (II):

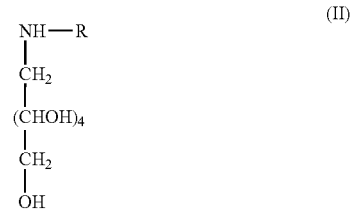

wherein:  
  R is selected from the group consisting of ethyl, propyl, butyl.

23 Claims, No Drawings

SALTS AND MIXTURE OF 9-OXOACRIDINE-10-ACETIC ACID WITH 1-ALKYLAMINO-1-DESOXY-POLYOLS, PHARMACEUTICAL COMPOSITIONS CONTAINING SAID AGENTS AND TREATMENT METHODS

This application is a 371 of PCT/RU2006/000614 filed on Nov. 17, 2006, published on May 24, 2007 under publication number WO 2007/058568 A2 which claims priority benefits from Russian Patent Application Number 2005136819 filed Nov. 21, 2005, the disclosure of which is hereby incorporated by reference.

The present invention relates to medicine and veterinary, in particular to medications containing N-acridonacetic acid, also known as (9-oxoacridine 10(9H)-yl)acetic acid, 9-oxo-10(9H)acridineacetic acid, or 2-(9-oxoacridin-10-yl)acetic acid, international non-proprietary name (INN) cridanimod, CAS 38609-97-1:

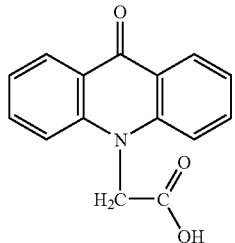

hereinafter, 9-oxoacridine-10-acetic acid and/or its salts.

Numerous antiviral and immunomodulating medications are known containing 9-oxoacridine-10-acetic acid salts, such as sodium salt (preparation Neovir, Register of Drugs of Russia, Drugs Encyclopedia, RDR-11th issue, Chief-Redactor Vishkovskiy A. L., Moscow, RDR-2004, 1503 pp.,), mixtures of 9-oxoacridine-10-acetic acid and salt-forming agent/solubilizer, for example, methylaminoalcohol (preparation Cycloferon containing 1-deoxy-1-(methylamino)-D-glucitol (Meglumine) as a solubilizer, Register of Drugs of Russia, Drugs Encyclopedia, RDR-11th issue, Chief-Redactor Vishkovskiy A. L., Moscow, RDR-2004, 1503 pp.) or N,N-dimethylaminoisopropylglucose, namely 3-O—(N,N-dimethylamino-n-propyl-1,2:5,6-di-O-isopropiliden-α-, D-glucofuranose (preparation Anandin, patent RU 2197248).

When some organic compounds are used as solubilizers for 9-oxoacridine-10-acetic acid in water solutions, either an individual chemical compound (a salt) is formed or a complex in the absence of formation of an individual chemical compound. In the latter case, often upon removal of the solvent from the solution, a solid residue is formed, which is a mechanical mixture of the two individual compounds, 9-oxoacridine-10-acetic acid and the solubilizer. The obtained solid residue has no distinct melting point and cannot be defined as an individual chemical compound. The said mixture of 9-oxoacridine-10-acetic acid and an organic base has limited solubility in aqueous solvents. A dynamic balance is established between dissociated molecules and non-dissociated ones. Moreover, molecules of starting substances possibly form complexes in water solutions as indicated by differences between IMR spectrum of the mixture comparing to the sum of IMR spectra of ingredients.

However, industrial applicability of salts and complexes of 9-oxoacridine-10-acetic acid and its medicinal preparations is hindered by its high physical-chemical instability due to the followings factors:

1) High photosensitivity of acridine skeleton of 9-oxoacridine-10-acetic acid, specific for all acridine-based compounds. In water solutions, acridine rings readily absorb UV irradiation and visible portions of the spectrum and undergo photoconversion with inactivation of 9-oxoacridine-10-acetic acid ions;

2) Intrinsic low solubility of 9-oxoacridine-10-acetic acid in non-ionic form requiring higher than physiologic pH levels, such as 8.0 and more, resulting in rapid decarboxylation of 9-oxoacridine-10-acetic acid to form 9-methyl-10-acridone.

Typically, to solve the above problems, stabilizing additives and pH-lowering buffer systems are introduced into the final formulation in addition to salt-formers and/or a solubilizers. Moreover, lowering of pH adjusts the acidity to values which are closer to physiologic ones. According to RU 2031650, TRIS base (tromethamine) and disodium salt of EDTA (trilon B) are added to the final formulation for these purposes. It is also proposed adding a buffer system based on citric acid and its sodium salt to the final formulation of sodium salt of 9-oxoacridine-10-acetic acid (preparation Neovir, Register of Drugs of Russia, Drugs Encyclopedia, RDR-11th issue, Chief-Redactor Vishkovskiy A. L., Moscow, RDR-2004, 1503 pp.) According to RU 2020941, in addition to citrate buffer, N, N,N',N',-tetramethylthionine chloride is added to a final formulation of sodium salt of 9-oxoacridine-10-acetic acid with the ratio "acridine derivative"/"N,N,N',N',-tetramethylthionine chloride" as 1:0.001-0.01). In this case N,N, N',N',-tetramethylthionine chloride served as internal photo-filter protecting the molecule of active moiety from light.

A considerable number of drugs containing salts and complexes formed by 9-oxoacridine-10-acetic acid and various salt-formers and solubilizers has been proposed over a period of several years, including amino sugars (RU 2036198) and its mono-substituted ethers (RU 2197248). Further, a number of drugs are known, comprising salts formed by 9-oxoacridine-10-acetic acid and 1-deoxy-1-N-methylaminohexaalcohols (RU 2135474). To reduce photodestructive processes, increase thermostability and raise the biological activity, RU 2182004 proposes adding to the water solution of a salt formed by 9-oxoacridine-10-acetic acid and N-methyl-D-glucamine, (i.e. to a solution of 1-deoxy-1-N-[methyl-(2-acri-9-on-10-yl-acetate)]-ammonium D-glucitol) a certain amount of a second salt-forming compound itself (i.e. N-methyl-D-glucamine) as a stabilizer. In this case, the preparation contains from 8.5 to 25.0% by mass of 1-deoxy-1-N-[methyl-(2-acri-9-on-10-yl-acetate)]-ammonium D-glucitol, from 0.05 to 1.0% by mass of N-methylglucamine, and balance water for injection. Hence, the water solution of the above preparation contains non-equimolar amounts of the salt-formers 9-oxoacridine-10-acetic acid, on the one hand, and N-methyl-D-glucamine on other hand, and thus, there is a surplus of the solubilizer/salt-former N-methyl-D-glucamine.

It shall be appreciated that excellent solubilizing properties of amino sugars (including amino alcohols) and its ethers are due primarily to high number of hydroxyl groups in its molecular structures.

Thus, the use of low-molecular organic or non-organic salt-formers in a final formulation results in considerable rise of osmolarity of water solution of a salt or complex, due to intrinsic osmotic activity of the salt-formers. That results in local pain when the preparation is administered parenterally, especially subcutaneously or intramuscularly. When higher molecular mass (more than 150 Da) organic compounds, such as linear or cyclic amino sugars and its ethers, are used as solubilizers for 9-oxoacridine-10-acetic acid and/or as stabilizers for water solutions thereof, osmolarity is reduced, though viscosity is raised. The increased viscosity causes difficulties in ultrafiltration and ampouling during manufacture. Further problems include reduced shell-life caused by instability of the preparations during storage, especially cold storage, when 9-oxoacridine-10-acetic acid can partially convert to the protonated form and form insoluble sediment rendering preparations unusable in clinics.

Moreover, the use of organic salts-/complex-formers of higher molecular mass in considerable mass quantities comparable with mass quantities of 9-oxoacridine-10-acetic acid itself in the final formulation, results in significant reduction of absorption rate of 9-oxoacridine-10-acetic acid at the site of intramuscular and/or subcutaneous injection and/or in slowing down the dissociation of "solubilizer-9-oxoacridine-10-acetic acid" complex formed when the preparation is administered intravenously or orally. Viscous organic solubilizer plays in part the role of a "depo" when it is injected intramuscularly and/or subcutaneously. The absorption rate of the active moiety in blood at the injection site, or dissociation rate of a complex and release rate of 9-oxoacridine-10-acetic acid ion following intramuscular injection or following oral administration, plays key role in attaining pharmacological effect of 9-oxoacridine-10-acetic acid and its salts. This is due primarily to the fact that 9-oxoacridine-10-acetic acid acts as inducer of interferons and other cytokines (providing the main immunomodulating and antiviral properties of compounds of 9-oxoacridine-10-acetic acid) based on "all or nothing" principle. In other words, it is essential for the achievement of the biological effect to build-up a certain minimal (threshold) level of dissociated form of 9-oxoacridine-10-acetic acid in short time period in the vicinity of a target cell.

9-oxoacridine-10-acetic acid is removed very rapidly in unaltered form by kidneys (e.g., the period of semi-elimination of its sodium salt from blood following intravenous injection does not exceed 30 minutes). Difference in rates of absorption of 9-oxoacridine-10-acetic acid at the site of intramuscular or subcutaneous injection (or its release from the "solubilizer-9-oxoacridine-10-acetic acid" complex following an intravenous injection or an oral administration) on the one hand, and elimination of its ionized form from blood on other hand, is the factor of crucial importance in the achievement of the therapeutically effective level of the active moiety in blood and tissues. Thus, the rate, with which the concentration of active ingredient rises to maximum concentration ($T_{max}$), following the administration of a preparation of 9-oxoacridine-10-acetic acid, determines in many respects whether biological/pharmacological properties of compounds based on 9-oxoacridine-10-acetic acid can be manifested in full scope.

RU 2135474 disclosing salts formed by 1-deoxy-1-N-methylaminohexaalcohols and N-acridonacetic (i.e. 9-oxoacridine-10-acetic) acid and medicinal compositions, can be regarded as closest prior art for the present invention.

The above prior art suffers from a number of disadvantages.

With respect to biological and pharmacological properties, the compounds disclosed in RU 2135474 exhibit insufficient ability to penetrate into cells, which is one of the most important factors, since the biological effects of 9-oxoacridine-10-acetic acid compounds are related to their ability to interact with internal cell substrates including DNA.

With respect to its physicochemical properties, the possible drawbacks of a water solution according to RU 2135474 could be the formation of a product of decarboxilation of 9-oxoacridine-10-acetic acid (9-methyl-10-acridone) and photodestruction of acridine skeleton of 9-oxoacridine-10-acetic acid.

Further, with respect to its clinical pharmacokinetic and pharmacologic properties, the compounds and compositions disclosed in RU 2135474 exhibit low absorption rate of active moiety of 9-oxoacridine-10-acetic acid from intramuscular or subcutaneous injection site into the bloodstream; low release rate of 9-oxoacridine-10-acetic acid from its bond created by the salt-former and inadequate distribution of the active moiety between blood and tissues after intravenous and oral administration; low penetration of the active ingredient into tissues after local application. The above prior art compounds further possess low ability for interferon induction and low cytokines release in humans and animals, and has low clinical efficacy with respect to a rather narrow spectrum of diseases which could be effectively treated.

The object of the present invention is to provide a new low-toxic remedy on the basis of 9-oxoacridine-10-acetic acid, which would be more effective in clinical practice, stable in manufacture and storage, possess better pharmacokinetic and pharmacodynamic properties, and suitable for prophylaxis and treatment of a number of immunopathologic, parasitic, dystrophic (degenerative), viral, bacterial, fungal, tumorous diseases and pathological conditions in humans and animals.

The problem posed by the present invention is solved by provision of novel salts and mixtures based on 9-oxoacridine-10-acetic acid in combination with a salt-forming/complexing agent or in admixture with 1-alkylamino-1-deoxypolyols of the general formula (II)

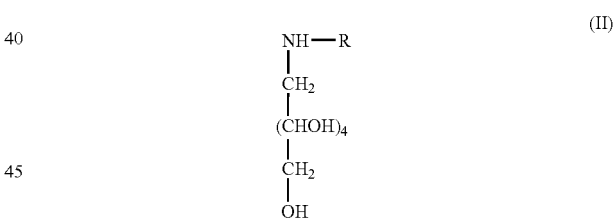

wherein R is selected from ethyl, propyl, butyl.

The invention further provides medicinal preparations comprising as an active ingredient the above defined mixture and salts (and their combinations) having the activity selected from the following: immunocorrecting, immunomodulating, antiviral, antibacterial (including anti-chlamydia), antiphlogistic, antiparasitic, antifungal, antitumor, radioprotective, stressprotective, and suitable for treatment, prophylaxis or correction of the following groups of diseases and conditions: immunodeficiency, viral infections, fungal infections, bacterial infections (including *Chlamydia*-caused infections), parasitic invasion, inflammatory processes, tumor diseases, degenerative inflammatory diseases of joints (arthroses), toxic conditions caused by chemo- and/or radio-therapy.

Further, the invention provides pharmaceutical dosage forms comprising the above compositions and mixtures, suitable for parenteral, local, oral and other methods of administration.

The experiments conducted by the inventors of the present invention in the development process have shown that the increase of hydrophobic properties of a salt-forming agents selected from the said group of 1-alkylamino-1-deoxypolyols (due to lengthening of aliphatic hydrocarbon chain of a substitute at the amino nitrogen atom in homologous series "ethyl-propyl-butyl") results in obvious reduction of the ability of corresponding 1-alkylamino-1-deoxypolyol to solubilize 9-oxoacridine-10-acetic acid of formula (III):

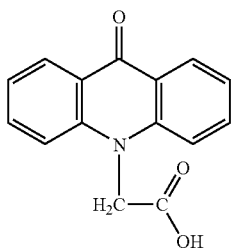

(III)

in water solution. On other hand, surprisingly, the considerable improvement of pharmacodynamic properties of the medicinal preparation and the increase in its pharmacological efficacy with reduction of side effects when the medicinal preparation is administered parenterally and locally (including rectally and intravaginally) and orally was observed.

Comparative tests showed that the claimed compounds and the claimed medicinal preparation were much more active/effective than the prior art compounds and compositions both in test-systems and in clinic practice. Moreover, it was surprisingly revealed that the claimed salts and mixtures not only possess less toxicity in comparison to the prototype (in corresponding molar ratio of 9-oxoacridine-10-acetic acid and respective salt-forming/complexing agent) but also have different spectrum of biological properties that was not characteristic neither for parent compounds taken separately, nor for the prototype. Furthermore, the relationship between the length of the aliphatic substitute radical at the amino nitrogen atom of 1-alkylamino-1-deoxypolyol in homologous series "ethyl-propyl-butyl" and different types and degree of biological/pharmacological activity, was surprisingly revealed.

The attempts of further lengthening of aliphatic "tail" of alkylaminogroup (5 carbon atoms and more) of a 1-alkylamino-1-deoxypolyol leads to drastic falling of solubility of a salt/complex in aqueous medium. At the same time, its stability decreases, making it impossible to produce the parenteral final formulation with acceptable volume of a single dose of the medicinal preparation; the salts/mixture toxicity increases as well.

Thus, according to the present invention, there are provided:

A) Salts of 1-alkylamino-1-deoxypolyols and 9-oxoacridine-10-acetic acid of the general formula (I):

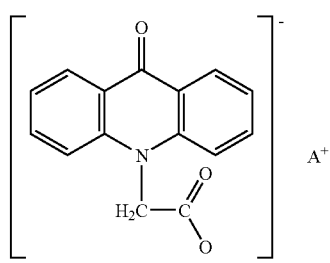

(I)

wherein:

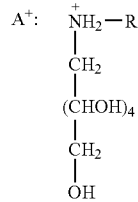

wherein R is selected from the group consisting of ethyl, propyl, butyl.

B) Salts of formula (I) possessing immunomodulating, immunocorrecting, antiparasitic, antisclerotic, antiviral, antibacterial including anti-chlamydia, antifungal, antiphlogistic, antitumor, radioprotective, stressprotective activities.

C) A medicinal preparation possessing immunomodulating, immunocorrecting, antiparasitic, antisclerotic, antiviral, antibacterial, antifungal, antiphlogistic, antitumor, radioprotective, stressprotective effects and comprising as the active agent novel salts of formula (I) (as well as their combination), an also mixtures of the above mentioned salt of the formula (I) and/or 9-oxoacridine-10-acetic acid of the formula (III):

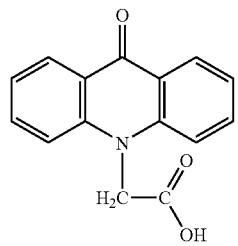

(III)

and one or more 1-alkylamino-1-deoxypolyols of the general formula (II):

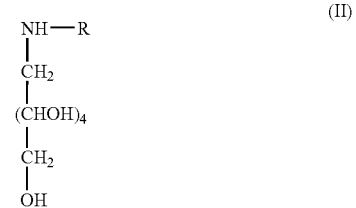

(II)

wherein:
R is selected from the group including ethyl, propyl, butyl, (and combinations thereof).

The above mentioned medicinal preparation can be realized in various embodiments as defined in the attached claims, for example, the medicinal preparation can comprise:

(a) 9-oxoacridine-10-acetic acid salt which is a compound of the formula (I);

(b) a mixture of 9-oxoacridine-10-acetic acid of formula (III) and 1-alkylamino-1-deoxypolyols of the general formula (II);

(c) a mixture of a salt of the formula (I) and 1-alkylamino-1-deoxypolyols of the general formula (II);

(d) a mixture of a salt of the formula (I) and 9-oxoacridine-10-acetic acid of the formula (III) and 1-alkylamino-1-deoxypolyols of the general formula (II).

Typically, to prepare a medicinal preparation and its dosage forms based on above defined mixtures of 1-alkylamino-1-deoxypolyols of the formula II and 9-oxoacridine-10-acetic acid, the ingredients of the mixture were blended in a near-equimolar ratio, however in certain embodiments, one of the ingredients was taken in considerable excess.

Moreover, the inventors of the present invention have shown that the use of a mixture of solubilizer/salt-forming agent of the formula II in different ratios for the preparation of the claimed medicinal preparation further increases photostability of 9-oxoacridine-10-acetic acid molecule and/or augments clinical efficacy of the claimed medical product.

The photostability of the claimed medicinal preparation was tested using a mercury quartz lamp at emissive power $5.2 \times 10^{-5}$ mWt/sec·square meter and layer thickness of 1 cm of 0.2 M solutions in quartz cuvette and at wavelength of 250-310 nm. An amount of the unaltered photosensitive moiety (9-oxoacridine-10-acetic acid) was determined by HPLC (high-performance liquid chromatography) using Shimadzu LC-6A chromatograph, chromatographic column Separon SGX C18 (5 micron, 3×150 mm (Tessex)) and spectrophotometer SPD-6AV at wavelength of 254 nm. Photostability data obtained for the tested solutions are presented in Table No. 1.

TABLE No. 1

Photostability data for the prototype and the inventive medicinal preparation.

| Exposition time (quartz lamp), hrs. | Percentage of 9-oxoacridine-10-acetic acid in the claimed medicinal preparation (% of basic amount). | Percentage of 9-oxoacridine-10-acetic acid in the prototype (% of basic amount). |
| --- | --- | --- |
| 0 | 100 | 100 |
| 0.5 | 99 | 93 |
| 1 | 96 | 85 |
| 2 | 97 | 74 |
| 4 | 96 | 60 |
| 6 | 96 | 53 |
| Conclusion on photostability | stable | not stable |

According to a preferred embodiment of the invention, a medicinal preparation is prepared in the form (a) as defined above and comprises N-(1-deoxy-D-glicitol-1-yl)-N-ethylammonium 9-oxoacridine-10-ylacetate as a salt of formula (I).

According to another preferred embodiment of the invention, a medicinal preparation is prepared in the form (b) as defined above and comprises a mixture of 9-oxoacridine-10-acetic acid and 1-deoxy-1-(ethylamino)-D-glucitol.

According to still another embodiment of the invention, one of preferred variants is a medicinal preparation defined as (c) above and comprising a mixture of N-(1-deoxy-D-glicitol-1-yl)-N-ethylammonium 9-oxoacridine-10-ylacetate and 1-deoxy-1-(ethylamino)-D-glucitol.

According to still another embodiment of the invention, one of preferred variants is a medicinal preparation defined as (d) above and containing a mixture of 9-oxoacridine-10-acetic acid and N-(1-deoxy-D-glicitol-1-yl)-N-ethylammonium 9-oxoacridine-10-ylacetate and 1-deoxy-1-(ethylamino)-D-glucitol.

The ratios of 9-oxoacridine-10-acetic acid, 1-alkylamino-1-deoxypolyol, alkylaminoalcohol in above mentioned mixtures (b), (c) and (d) may considerably vary depending on the type of the mixture and, correspondingly, preferably is within the following limits:

(b) from 1.2:1 to 1:1.1;
(c) from 220:1 to 5.5:1;
(d) (1-100):(1-100):(1-100) and can be determined by a specialist depending on specific situation.

At the same time, it have to be taken into consideration that amounts of above mentioned ingredients in the medicinal preparation may considerably vary depending on the intended purpose of a medicinal preparation (for example, treatment or prophylaxis), on its dosage form (for example, for parenteral or oral use or for other route of administration) as well as on a method of treatment (single-dose or course treatment) etc.

Precise amounts of ingredients, for each particular case, can be calculated by a specialist on the basis of the following detailed description of the invention and illustrative embodiments which do not limit the scope of the invention.

D) Dosage form of the present medicinal preparation which are designed for parenteral, local, oral, rectal, intravaginal, intracavitary and for other routes of administration.

In one of the embodiments of the invention a dosage form suitable for parenteral use comprises above mentioned salts of the formula (I) or the mixtures (b), (c) or (d) in amount, preferably from 9.0 to 28.0 mass % (solid residual) and the rest is water for injection.

Moreover, the dosage form suitable for parenteral route may additionally comprise additives, for example, a diluent, a thickener, an internal color filter (for example N,N,N', N',-tetramethylthionine chloride) and other common agents, suitable for production of parenteral preparations or modification of their properties, for example cyclodextrins like hydroxypropyl-β-cyclodextrin or other modified cyclodextrins. Thus, for example, in some cases, to adjust pH to physiological level as well as to increase stability of dosage forms, inorganic and/or organic bases which may be added as extra ingredients into the medicinal preparation formulation and which are broad used for this purpose in pharmaceutics, for example, alkali element hydroxides and/or tertiary, secondary and quaternary amines (as β-diethanolamine; 1,2-ethylenediamine; tris(hydroxymethyl)aminomethane (tromethamine); diethylamine; hydrabamine; ethanolamine; triethanolamine; glucamine; 2-(4-imidazolyl)-ethylamine; choline; arginine and their stereoisomers, etc).

Further, in other embodiment of the present invention, a dosage form suitable for local (topic) use may be an emulsion, a gel, a cream, a liniment, etc.

The dosage form for local use may comprise above mentioned salts of the formula (I) or the mixtures (b), (c) or (d) in amount, preferably from 5.0 mass. % to 90.0 mass %, and may have cream, ointment or gel base.

Further, in another embodiment of the present invention, a dosage form suitable for oral use may be a tablet (including an enteric-coated film tablet), as well as a capsule, a granule, a suspension, a solution, etc.

The dosage form for oral use comprises above mentioned salts of the formula (I) or the mixtures (b), (c) or (d) in amount, preferably from 20 mass.% to 99.9 mass %.

The single dosage form for oral use may comprise a dose from 0.5 to 30 mg/kg of body weight, preferably from 2 to 10 mg/kg (i.e., for example, from 120-160 mg to 600-800 mg for a subject of 60-80 kg body weight).

Further, according the invention, a dosage form suitable for rectal and/or intravaginal use may be a suppository, a liniment, a cream, a gel, an emulsion, a suspension, etc. It is preferably that the dosage form suitable for rectal and/or intravaginal use comprises above mentioned salts of the formula (I) or the mixtures (b), (c) or (d) in amount, preferably from 5.0 mass. % to 90.0 mass %. The single dosage form for rectal and/or intravaginal use (suppository) may comprise a dose from 2 to 10 mg/kg of body weight (i.e., for example, from 120-160 mg to 600-800 mg for a subject of 60-80 kg body weight).

E) Further, the present invention provides use of a salt of formula (I) and/or mixture 9-oxoacridine-10-acetic acid or a salt of formula (I) and one or more 1-alkylamino-1-deoxy-polyols of general formula (II), or their pharmaceutically acceptable derivates or precursors, or pharmaceutical preparation containing their, for treatment and prophylaxis of diseases and pathological conditions of humans and animals.

In particular, it is provided the use above mentioned salts and mixtures and medications on their bases, for prevention or treatment of diseases and/or conditions associated with or accompanied by immunologic status alteration, for example, including (but not limited to) the followings: HIV-infection; neuroinfection including meningitis and encephalitis; vital hepatitis A or B and/or C and/or D; herpes and/or cytomegalovirus infection; infectious mononucleosis; immunodeficiency including secondary immunodeficiency concerned with trauma, viral and/or bacterial and/or fungal infections and or parasitic invasions; parasitic invasions; bacterial infection including *Chlamydia* infection; systemic rheumatic and connective tissue diseases, including rheumatoid arthritis; degenerative inflammatory diseases of joints, including secondary and primary osteoarthritis; prostatitis; oncologic diseases; pathological conditions caused by chemotherapy and/or exposure to radiation. The above mentioned salts, mixture and medications containing theirs may be used for treatment and prophylaxis diseases and/or pathological conditions of humans and animals.

F) Further, the present invention provides methods of treatment and prophylaxis of wide range of diseases and pathological conditions of infectious and non-infectious nature, using the claimed medical product, in particular, of treatment and prophylaxis of conditions concerned with immunologic status alteration, of treatment and prophylaxis of systemic rheumatic and connective tissue diseases, including but not limited to rheumatoid arthritis; degenerative inflammatory diseases of joints, including secondary and primary osteoarthrosis; viral infection, including but not limited to HIV-infection; vital hepatitis A or B and/or C and/or D; herpes and/or cytomegalovirus infection; infectious mononucleosis; immunodeficiency including secondary immunodeficiency associated with trauma, viral and/or bacterial and/or fungal infections and or parasitic invasions; parasitic invasions; fungal diseases, including but not limited to onychomycosis, candidosis; bacterial infection including *Chlamydia* infection; prostatitis; oncologic diseases; as well as prophylaxis and correction of adverse events which are naturally appeared as effects of cytostatic therapy and/or radiotherapy.

In process of experimental and clinic studies, it were shown that the claimed compounds and the claimed medicinal preparation possess pronounced immunomodulating, immunocorrecting, antiparasitic, antisclerotic, antiviral, antibacterial, antifungal, antiphlogistic, antitumor, radioprotective, stressprotective action, and at the same time they have low toxicity, low adverse events rate, high stability.

Biologic/pharmacologic activity and toxicity of the new claimed compounds including their ability to penetrate into/bind to cell structures were investigated in comparison with the prototype in different test-systems. The claimed compounds have better ability to penetrate into/to bind to cell structures, as shown by comparison with the prototype and illustrated by Table No. 2.

TABLE No. 2

The claimed compounds penetration/binding to different type cells in comparison with the prototype

| | Cells | | |
|---|---|---|---|
| Preparation | Human peripheral blood lymphocytes | Human breast cancer cell line D-1 | Human hepatoma cell line HepG-2 |
| | Induced acridine nucleus fluorescence in washed cells* | | |
| The claimed compound No. 1 (R = ethyl) | 3.27 | 2.92 | 3.00 |
| The claimed compound No. 2 (R = propyl) | 5.1 | 4.59 | 4.27 |
| The claimed compound No. 3 (R = butyl) | 8.37 | 6.98 | 6.28 |
| The prototype | 1.52 | 1.24 | 1.11 |
| Sodium salt of 9-oxoacridine-10-acetic acid | 1.00 | 1.00 | 1.00 |

*The fluorescence value of samples with inorganic (sodium) salt of 9-oxoacridine-10-acetic acid were taken as 1.00 for corresponding cell type in corresponding series for each type of cells.

Acute toxicities ($DL_{50}$) of the claimed compounds in mice after intraperitoneal injection were calculated by the Litchfield and Wilkinson probit and they were from 500 to 650 mg/kg. At the same time the prototype toxicity ($DL_{50}$) was 450 mg/kg and it said that the prototype was more toxic than the claimed compounds.

According to the invention the claimed method of treatment and prophylaxis of the diseases includes as single dose or single introduction as the course of treatment, i.e. repeated doses and/or repeated introductions during some period of time.

The claimed medicinal preparation may be administered once a day or several times per day. Preferred single dose of the claimed medicinal preparation, calculated as 9-oxoacridine-10-acetic acid or its residue, is from 0.5 to 20 mg/kg of body weight, more preferred single dose is from 3 to 10 mg/kg of body weight.

To administer the claimed medicinal preparation parenterally and orally, one of preferred treatment regimens is the course contained from 5 to 12 introductions at days 1, 2, 4, 6, 8, 11, 14, 17, 20, 23, 26, 29. According to another possible treatment regimen, the courses are repeated with an interval, for example, from 10 to 14 days.

It is possible to repeat the course of treatment not less than twice.

According to the invention, the medicinal preparation may be used as a monotherapeutic agent and also as a constituent of complex and/or combined therapy. For example the preparation may be effective as a component of complex therapy: of HIV-infection (for example, in combination with nucleoside-based pharmaceuticals like azidothymidine and/or with reverse transcriptase inhibitors and/or with biotechnologically produced proteins, for example, with monoclonal antibodies or vaccines), of bacterial and/or fungal infection (for example, in combination with antibiotics or chemical agents including fluoroquinolones), of viral hepatitis (for example, in combination with ribavirine and\or with interferons and\or with cytokines and/or with biotechnologically produced proteins, for example, with monoclonal antibodies or vaccines), of tumor diseases (for example, in combination with cytostatics and/or hormones or their antagonists and/or with biotechnologically produced proteins, for example, with monoclonal antibodies or therapeutic vaccines and also in combination with surgical treatment including the use of adjuvant and/or neo-adjuvant regimens.

As shown in the presented examples, the inventive salts of 9-oxoacridine-10-acetic acid have higher biological and pharmacological activity than the prototype with a lesser number of negative/adverse effects. At the same time the claimed compounds ability to penetrate into tissue and cells is considerable higher, and range of biological and pharmacological activity is wider than those of prototype.

TABLE No. 3

The penetration of the claimed compound into tissue following topical application in an inert vehicle

| Compound | Concentration in tissues (average). |
|---|---|
| The claimed compound No. 1 | 3.27 mkg/kg |
| The claimed compound No. 2 | 4.03 mkg/kg |
| The prototype | 1.60 mkg/kg |

The investigation of pharmacokinetic and pharmacodynamic characteristics and clinical efficacy and safety of different dosage forms of the claimed medicinal preparation showed that the claimed medicinal preparation possesses better pharmacokinetic and pharmacodynamic characteristics and also increased clinical efficacy with a lesser number of negative/adverse effects as compared with those of prototype.

The table No. 4 presents the data of pharmacodynamic and pharmacokinetic studies of the claimed medicinal preparation in comparison with the prototype.

In the course of work on the invention the authors also developed the parenteral dosage forms of the claimed medicinal preparation as its variants which contain 9-oxoacridine-10-acetic acid and a solubilizer/salt-former namely 1-deoxy-1-(ethylamino)-D-glucitol. Taking into account a clinically relevant, effective single dose of the preparation which was from 2 to 10 mg/kg of body weight (calculated as 9-oxoacridine-10-acetic acid), and a maximum permissible volume of parenteral, in particular, intramuscular injection, the mass fraction of the dry matter and the mixture components ratios were determined, and the photostability examinations of the developed parenteral dosage form were carried out.

The safety (local irritant effect) was evaluated following the intramuscular injection of preparations with different components ratios, into femoral muscle of beagle dogs weighing 10-11 kg. The local irritant effect was evaluated on the basis of development and degree of inflammatory reaction following intramuscular injection of 4 ml of the preparation, by observation of behavioral response to the injection and by histological examination of the tissues at the injection site.

Photostability was assessed on the basis of a reduction of percentage of photosensitive component in the dosage form (9-oxoacridine-10-acetic acid) after exposition of samples to ultraviolet light with wavelengths of 350-450 nm. An amount of 9-oxoacridine-10-acetic acid was determined by high-performance liquid chromatography using Shimadzu LC-6A chromatograph, chromatographic column Separon SGX C18

TABLE No. 4

Pharmacokinetic and pharmacodynamic properties of the claimed medicinal preparation following intramuscular injection compared with the prototype.

| | parameter | | | |
|---|---|---|---|---|
| Preparation | $C_{max}$, mkg/ml | $T_{max}$, hrs | Alpha-interferon level observed 2.5 h after injection, relative units, mean ± st. deviation | Phagocytic index of peripheral blood polymorphonuclear leucocytes observed 3 day after injection, relative units, mean ± st. deviation |
| The claimed medicinal preparation | 65.6 ± 7.0 | 0.51 ± 0.07 | 6.4 ± 1.1 | 59 ± 5 |
| The prototype | 54.1 ± 5.2 | 0.67 ± 0.05 | 4.4 ± 0.8 | 43 ± 7 |

* The preparations were administered in healthy volunteers, once intramuscularly in a dose of 8 mg/kg of body weight (calculated as 9-oxoacridine-10-acetic acid)

The claimed medicinal preparation based on the new claimed salts and mixtures showed its efficacy as treatment and prophylaxis remedy for a wide range of diseases of viral, parasitic, bacterial (including *Chlamydia*), fungal, tumor, inflammatory, degenerative-dystrophic origin, as well as for correction of pathological conditions associated directly or indirectly with alterations in immune status.

(5 micron, 3×150 mm (Tessex)) and spectrophotometer SPD-6AV at wavelength of 254 nm. A dosage form was considered as photostable if an amount of photosensitive component to be evaluated (9-oxoacridine-10-acetic acid) was reduced no more than 20% after 4 hours' exposition. The data on physicochemical and pharmacological properties of the developed dosage form are presented in Table No. 5.

TABLE No. 5

Characteristics of variants of the parenteral dosage form of the claimed medicinal preparation with different ratios of mixture components "9-oxoacridine-10-acetic acid:1-deoxy-1-N-ethylamino-D-glucitol" and with different water content.

| Content of water for injection, % | Weight ratio of mixture components <<9-oxoacridine-10-acetic acid:1-deoxy-1-N-ethylamino-D-glucitol>> | Appearance | Local irritant activity | Sufficiency of effective dose in highest possible volume of intramuscular or bolus intravenous injection. | Photosatbility | Acceptability of acidity of preparation for parenteral use (pH 7.2-7.8) |
|---|---|---|---|---|---|---|
| 92.0 | 1.3:1 | Suspended matter | Yes | Insufficient | Non-stable | Unacceptable |
| | 1.2:1 | Clear solution | No | Insufficient | Stable | Acceptable |

TABLE No. 5-continued

Characteristics of variants of the parenteral dosage form of the claimed medicinal preparation with different ratios of mixture components "9-oxoacridine-10-acetic acid:1-deoxy-1-N-ethylamino-D-glucitol" and with different water content.

| Content of water for injection, % | Weight ratio of mixture components <<9-oxoacridine-10-acetic acid:1-deoxy-1-N-ethylamino-D-glucitol>> | Appearance | Local irritant activity | Sufficiency of effective dose in highest possible volume of intramuscular or bolus intravenous injection. | Photosatbility | Acceptability of acidity of preparation for parenteral use (pH 7.2-7.8) |
|---|---|---|---|---|---|---|
| | 1.1:1 | Clear solution | No. | Insufficient | Stable | Acceptable |
| | 1:1 | Clear solution | No | Insufficient | Stable | Acceptable |
| | 1:1.1 | Clear solution | No | Insufficient | Stable | Acceptable |
| | 1:1.2 | Clear solution | Yes | Insufficient | Stable | Unacceptable |
| 91.0-72.0 | 1.3:1 | Suspended matter | No | Sufficient | Non-stable | Acceptable |
| | 1.2:1 | Clear solution | No. | Sufficient | Stable | Acceptable |
| | 1.1:1 | Clear solution | No | Sufficient | Stable | Acceptable |
| | 1:1 | Clear solution | No | Sufficient | Stable | Acceptable |
| | 1:1.1 | Clear solution | No | Sufficient | Stable | Acceptable |
| | 1:1.2 | Clear solution | Yes | Sufficient | Stable | Unacceptable |
| 71.0 | 1.3:1 | Viscous suspended matter | Yes | Sufficient | Non-stable | |
| | 1.2:1 | Viscous liquid with crystals | Yes | Sufficient | Stable | |
| | 1.1:1 | Viscous liquid with crystals | Yes | Sufficient | Stable | |
| | 1:1 | Viscous liquid with crystals | Yes | Sufficient | Stable | |
| | 1:1.1 | Viscous liquid with crystals | Yes | Sufficient | Stable | |
| | 1:1.2 | Viscous liquid with crystals | Yes | Sufficient | Stable | |

The preparation was a viscous liquid when water content was less than 72 percent. When such preparation was injected the considerable reaction of inflammation and oedema was appeared, besides, the animals responded to injection with licking of injection site and with vocalization (whimper). At the same time if mass fraction of 9-oxoacridine-10-acetic acid was higher than those of 1-deoxy-1-N-(ethylamino)-D-glucitol the preparation represented itself a viscous liquid with crystals of non-solubilized 9-oxoacridine-10-acetic acid and its pH values were far from physiologic ones.

If mass fraction of 1-deoxy-1-N-(ethylamino)-D-glucitol was more than 1.1 times higher than those of 9-oxoacridine-10-acetic acid the preparation showed high values of $T_{max}$ and low values of $C_{max}$, induced low interferon response after parenteral administration and has high non-physiological pH. When mass fraction of 9-oxoacridine-10-acetic acid was more than 1.2 times higher than those of 1-deoxy-1-N-(ethylamino)-D-glucitol the preparation became non-photostable.

It emerged that optimal weight ratio of components of the mixture "9-oxoacridine-10-acetic acid:1-deoxy-1-N-(ethylamino)-D-glucitol" is ratio from 1.2:1 to 1:1.1 with minimal water content of 72.0 mass % and maximal water content of 91.0 mass % in the dosage form for parenteral use.

Another variant of the parenteral dosage form of the claimed medicinal preparation was obtained by initial dilution N-(1-deoxy-D-glucitol-1-yl)-N-ethyl ammonium 9-oxoacridine-10-ylacetate in water for injection with following addition of 1-deoxy-1-(ethylamino)-D-glucitol.

It emerged that optimal weight ratio of components of the mixture "N-(1-deoxy-D-glucitol-1-yl)-N-ethyl ammonium 9-oxoacridine-10-ylacetate:1-deoxy-1-(ethylamino)-D-glucitol" is ratio from 220:1 to 5.5:1 with minimal water content of 72.0 mass % and maximal water content of 91.0 mass % in the dosage form for parenteral use. As this variant of parenteral dosage form was developed the inventors controlled characteristics according to the same parameters. The data are presented in Table No. 6.

TABLE No. 6

Characteristics of variants of the parenteral dosage form of the claimed medicinal preparation with different ratios of mixture components "N-(1-deoxy-D-glucitol-1-yl)-N-ethyl ammonium 9-oxoacridine-10-ylacetate:1-deoxy-1-(ethylamino)-D-glucitol" and with different water content.

| Content of water for injection, % | Weight ratio of mixture components "N-(1-deoxy-D-glucitol-1-yl)-N-ethyl ammonium 9-oxoacridine-10-ylacetate:1-deoxy-1-(ethylamino)-D-glucitol" | Appearance | Local irritant activity | Sufficiency of effective dose in highest possible volume of intramuscular or bolus intravenous injection. | Photosatbility | Acceptability of acidity of preparation for parenteral use (pH 7.2-7.8) |
|---|---|---|---|---|---|---|
| 92.0 | 240:1 | Suspended matter | Yes | Insufficient | Non-stable | Unacceptable |
| | 220:1 | Clear solution | No | Insufficient | Stable | Acceptable |
| | 20:1 | Clear solution | No | Insufficient | Stable | Acceptable |
| | 10:1 | Clear solution | No | Insufficient | Stable | Acceptable |
| | 5.5:1 | Clear solution | No | Insufficient | Stable | Acceptable |
| | 5:1 | Clear solution | Yes | Insufficient | Stable | Unacceptable |
| 91.0-72.0 | 240:1 | Suspended matter | No | Sufficient | Non-stable | Acceptable |
| | 220:1 | Clear solution | No | Sufficient | Stable | Acceptable |

TABLE No. 6-continued

Characteristics of variants of the parenteral dosage form of the claimed medicinal preparation with different ratios of mixture components "N-(1-deoxy-D-glucitol-1-yl)-N-ethyl ammonium 9-oxoacridine-10-ylacetate:1-deoxy-1-(ethylamino)-D-glucitol" and with different water content.

| Content of water for injection, % | Weight ratio of mixture components "N-(1-deoxy-D-glucitol-1-yl)-N-ethyl ammonium 9-oxoacridine-10-ylacetate:1-deoxy-1-(ethylamino)-D-glucitol" | Appearance | Local irritant activity | Sufficiency of effective dose in highest possible volume of intramuscular or bolus intravenous injection. | Photosatbility | Acceptability of acidity of preparation for parenteral use (pH 7.2-7.8) |
|---|---|---|---|---|---|---|
|  | 200:1 | Clear solution | No | Sufficient | Stable | Acceptable |
|  | 100:1 | Clear solution | No | Sufficient | Stable | Acceptable |
|  | 40:1 | Clear solution | No | Sufficient | Stable | Acceptable |
|  | 20:1 | Clear solution | No | Sufficient | Stable | Acceptable |
|  | 10:1 | Clear solution | No | Sufficient | Stable | Acceptable |
|  | 5.5:1 | Clear solution | No | Sufficient | Stable | Acceptable |
|  | 5:1 | Clear solution | Yes | Sufficient | Stable | Unacceptable |
| 71.0 | 240:1 | Viscous suspended matter | Yes | Sufficient | Non-stable | Acceptable |
|  | 220:1 | Viscous liquid with crystals | Yes | Sufficient | Stable | Acceptable |
|  | 20:1 | Viscous liquid with crystals | Yes | Sufficient | Stable | Acceptable |
|  | 10:1 | Viscous liquid with crystals | Yes | Sufficient | Stable | Acceptable |
|  | 5.5:1 | Viscous liquid with crystals | Yes | Sufficient | Stable | Acceptable |
|  | 5.:1 | Viscous liquid with crystals | Yes | Sufficient | Stable | Unacceptable |

In the pharmacokinetic study was shown that the plasma level of active moiety (measured as level of the acridine component) reaches its maximum more quickly, the value of maximal concentration is higher, and main biological/pharmacological effects is significantly more potent after administration of the claimed parenteral dosage form than after administration of the prototype.

Thus, the inventors additionally claimed as the variants of the claimed medicinal preparation the parenteral dosage forms with following components' ratio:

I: A mixture of 9-oxoacridine-10-acetic acid and 1-deoxy-1-N-(ethylamino)-D-glucitol with their weight ratio from 1.2:1 to 1:1.1:
9.0-28.0 mass %;
the rest is water for injection.

II. A mixture of N-(1-deoxy-D-glucitol-1-yl)-N-ethyl ammonium 9-oxoacridine-10-ylacetate and 1-deoxy-1-(ethylamino)-D-glucitol with their weight ratio from 1.2:1 to 1:1.1:
9.0-28.0 mass %;
the rest is water for injection.

The invention is illustrated by the following examples:

EXAMPLE 1

The Synthesis of the Claimed Compounds

A. Under intensive stirring, 25.3 g of 9-oxoacridine-10-acetic acid, 40 ml of distilled water and 0.1 mole (20.1 g) of 1-deoxy-1-N-(ethylamino)-D-glucitol are placed to a retort with backflow condenser. The mixture is boiled for 25-35 min., then it is cooled to room temperature and 100 ml of acetone is added with intensive stirring. The laid down sediment is filtered, washed by 50 ml of absolute ethanol and is dried under reduced pressure for 1 hour to provide in accordance with the selected 1-alkylamino-1-deoxypolyol:
N-(1-deoxy-D-glucitol-1-yl)-N-ethyl ammonium 9-oxoacridine-10-ylacetate (1)

| | N | H | C | Brutto formula |
|---|---|---|---|---|
| Found: | 6.08 | 6.57 | 59.95 | $C_{23}H_{30}N_2O_8$ |
| Calculated: | N | H | C | Mm = 462.49 |
| | 6.06 | 6.54 | 59.73 | |

NMR spectra ($D_2O$):
1.28 (3H, t, $CH_3$), 2.84-3.16 (4H, m, $CH_2$), 3.77-3.89 (6H, m, $CH_2$, CH), 4.10 (2H, s, $CH_2$), 7.23-7.58 (4H, m, Ar), 7.79-7.96 (2H, m, Ar), 8.22-8.39 (2H, m, Ar).

Melting point: 130-133° C.

B. 103.3 g of 1-deoxy-1-N-(propylamino)-L-galactitol is dissolved In 200 ml of water and then 125.3 g of well-milled powder of 9-oxoacridine-10-acetic acid is added in the solution, in small portions, under stirring until complete dissolution. 1000 ml of absolute ethanol is added. The laid down sediment is filtered washed on the filter by 150 ml of absolute ethanol and is dried under reduced pressure at 60° C. for 1 hour to provide in accordance with the selected 1-alkylamino-1-deoxypolyol:
N-(1-deoxy-D-galactitol-1-yl)-N-propyl ammonium 9-oxoacridine-10-ylacetate (2)

| | N | H | C | Brutto formula |
|---|---|---|---|---|
| Found: | 5.75 | 6.73 | 60.58 | $C_{24}H_{32}N_2O_8$ |
| Calculated: | N | H | C | Mm = 476.51 |
| | 5.78 | 6.77 | 60.49 | |

NMR spectra ($D_2O$):
1.28 (3H, t, $CH_3$), 1.84 (1H, m, $CH_2$), 2.38 (1H, q, $CH_2$), 2.84-3.16 (4H, m, $CH_2$), 3.77-3.89 (6H, m, $CH_2$, CH), 4.10 (2H, c, $CH_2$), 7.23-7.58 (4H, m, Ar), 7.79-7.96 (2H, m, Ar), 8.22-8.39 (2H, m, Ar).

Melting point: 127-130° C.

C) 100 g of 9-oxoacridine-10-acetic acid and 150 ml of distilled water are placed to a retort with backflow condenser and then 93.6 g of 1-deoxy-1-N-(butylamino)-D-mannitol is added under intensive stirring. The obtained mixture is boiled for 20 min until complete dissolution. The solution is cooled to 20-22° C. and mixed with 100 ml of acetone. The retort with laid down sediment is cooled in melting ice (0-1° C. for 4 hours. Then the sediment is filtered and washed on filter by 40 ml of cooled acetone and dried under reduced pressure at 60° C. to provide in accordance with the selected 1-alkylamino-1-deoxypolyol:

N-(1-deoxy-D-mannitol-1-yl)-N-butyl ammonium 9-oxoacridine-10-ylacetate (3)

| Found: | N | H | C | Brutto formula |
|---|---|---|---|---|
| | 5.74 | 6.95 | 61.15 | $C_{25}H_{34}N_2O_8$ |
| Calculated: | N | H | C | Mm = 490.55 |
| | 5.71 | 6.99 | 61.21 | |

NMR spectra ($D_2O$):
1.28 (3H, t, $CH_3$), 1.62-1.70 (1H, m, $CH_2$), 1.80-1.95 (2H, m, $CH_2$), 2.30 (1H, q, $CH_2$), 2.84-3.16 (4H, m, $CH_2$), 3.77-3.89 (6H, m, $CH_2$, CH), 4.10 (2H, s, $CH_2$), 7.23-7.58 (4H, m, Ar), 7.79-7.96 (2H, m, Ar), 8.22-8.39 (2H, m, Ar).

Melting point: 126-129° C.

Salts of 9-oxoacridine-10-acetic acid and D- and L-isomers of respective selected 1-alkylamino-1-deoxypolyols are obtained in a similar manner:

N-(1-deoxy-D-glucitol-1-yl)-N-propyl ammonium 9-oxoacridine-10-ylacetate (4);
N-(1-deoxy-D-glucitol-1-yl)-N-butyl ammonium 9-oxoacridine-10-ylacetate (5);
N-(1-deoxy-D-galactitol-1-yl)-N-ethyl ammonium 9-oxoacridine-10-ylacetate (6);
N-(1-deoxy-D-galactitol-1-yl)-N-propyl ammonium 9-oxoacridine-10-ylacetate (7);
N-(1-deoxy-D-galactitol-1-yl)-N-butyl ammonium 9-oxoacridine-10-ylacetate (8)
N-(1-deoxy-D-mannitol-1-yl)-N-ethyl ammonium 9-oxoacridine-10-ylacetate (9)
N-(1-deoxy-D-mannitol-1-yl)-N-propyl ammonium 9-oxoacridine-10-ylacetate (10)
N-(1-deoxy-L-glucitol-1-yl)-N-ethyl ammonium 9-oxoacridine-10-ylacetate (11)
N-(1-deoxy-L-glucitol-1-yl)-N-propyl ammonium 9-oxoacridine-10-ylacetate (12)
N-(1-deoxy-L-glucitol-1-yl)-N-butyl ammonium 9-oxoacridine-10-ylacetate (13)
N-(1-deoxy-L-galactitol-1-yl)-N-ethyl ammonium 9-oxoacridine-10-ylacetate (14)
N-(1-deoxy-L-galactitol-1-yl)-N-butyl ammonium 9-oxoacridine-10-ylacetate (15)
N-(1-deoxy-L-mannitol-1-yl)-N-ethyl ammonium 9-oxoacridine-10-ylacetate (16)
N-(1-deoxy-L-mannitol-1-yl)-N-propyl ammonium 9-oxoacridine-10-ylacetate (17)
N-(1-deoxy-L-mannitol-1-yl)-N-butyl ammonium 9-oxoacridine-10-ylacetate (18)

The yield of obtained compounds is 97-99%.

The dry forms of obtained salts presented themselves the light yellow crystallic powders which are hygroscopic, well soluble in water and in other polar solvents, and poorly soluble or insoluble in chloroform and in other non-polar solvents. Chromatographic purity of the obtained compounds is 97-99%.

EXAMPLE 2

The Preparation of the Medicinal Preparation for Parenteral Use, Comprising as Active Ingredient the Mixture of 9-oxoacridine-10-acetic Acid and 1-alkylamino-1-deoxypolyol 100.0 g of finely ground crystalline 9-oxoacridine-10-acetic acid is added to 300 ml of water for injection and then, under intensive stirring, 82.6 g of the solubilizer-1-deoxy-1-(ethylamino)-D-glucitol is added to the mixture. The mixture is stirred at room temperature for 2 hours until complete dissolution of all components. Then water for injection is added to volume of 1100-1200 ml. Then, to adjust pH solution to 7.4-7,8,1-deoxy-1-(ethylamino)-D-glucitol is additionally added in small portions, and water for injection is added for a volume of 1400 ml. The solution is filtered trough a sterilizing filter and dispensed into sterile 2 ml containers.

The obtained solution comprises 12.5 mass % of 9-oxoacridine-10-acetic acid, 10.5 mass % of 1-deoxy-1-(ethylamino)-D-glucitol and 77 mass % of water for injection.

EXAMPLE 3

The Preparation of the Medicinal Preparation for Parenteral Use, Comprising as Active Ingredient the Mixture of 9-oxoacridine-10-acetic acid and 1-alkylamino-1-deoxypolyol 12.5 kg of finely ground crystalline 9-oxoacridine-10-acetic acid is added to 80 l of water for injection and then, under intensive stirring, 110.3 kg of the solubilizer-1-deoxy-1-(propylamino)-D-glucitol is added in small portions to the mixture. The mixture is stirred at room temperature for 2 hours until complete dissolution of all components. Then water for injection is added to the total volume of 90 liter.

pH is checked and adjusted to 7.4-7.8 by adding of tris (hydroxymethyl)aminomethane (i.e. tromethamine) in small portions, and then water for injection was added to the total volume of 100 liter. The solution is filtered trough a sterilizing filter and dispensed into sterile 2 ml or 5 ml containers.

The obtained solution comprises 12.5 mass % of 9-oxoacridine-10-acetic acid, 11.03 mass % of 1-deoxy-1-(propylamino)-D-glucitol, 0.05-0.1% of tris(hydroxymethyl) aminomethane (i.e tromethamine), and the rest is water for injection.

EXAMPLE 4

The Preparation of the Medicinal Preparation for Parenteral Use, Comprising as Active Ingredient the Salt of 9-oxoacridine-10-acetic acid and 1-alkylamino-1-deoxypolyol 90 g of N-(1-deoxy-L-galactitol-1-yl)-N-propyl ammonium 9-oxoacridine-10-ylacetate is dissolved in 800 ml of water for injection. pH is checked and adjusted to 7.4-7.6 by adding of β-diethanolamine in small portions, and then water for injection is added to the total volume of 1000 ml. The solution is filtered trough a sterilizing filter and dispensed into sterile 2 ml or 5 ml containers.

The obtained solution comprises 9.0 mass % of N-(1-deoxy-L-galactitol-1-yl)-N-propyl ammonium 9-oxoacridine-10-ylacetate 0.02-0.5% of (3-diethanolamine, and the rest is water for injection.

EXAMPLE 5

The Preparation of the Medicinal Preparation for Parenteral Use, Comprising as Active Ingredient the Mixture of 9-oxoacridine-10-acetic acid and 1-alkylamino-1-deoxypolyol 12.5 kg of microcrystalline 9-oxoacridine-10-acetic acid is added to 70 l of water for injection and then, under intensive stirring, 23.4 kg of the solubilizer-1-deoxy-1-(butylamino)-D-glucitol is added in small portions to the mixture. The mixture is stirred at room temperature for 2 hours until complete dissolution of the components. Then water for injection is added to a volume of 100 liter. The solution is filtered trough a sterilizing filter and dispensed into sterile 2 ml or 5 ml containers.

The obtained solution comprises 12.5 mass % of 9-oxoacridine-10-acetic acid, 23.4 mass % of 1-deoxy-1-(butylamino)-D-glucitol, and the rest is water for injection.

EXAMPLE 6

The Preparation of the Medicinal Preparation for Parenteral Use, Comprising as Active Ingredient the Mixture of 9-oxoacridine-10-acetic acid and Two Different 1-alkylamino-1-deoxypolyols 4.85 kg of finely crystalline 9-oxoacridine-10-acetic acid is added to 70 l of water for injection and then, under intensive stirring, 4.16 kg of the mixture of solubilizers: 1-deoxy-1-(ethylamino)-D-glucitol and 1-deoxy-1-(propylamino)-D-glucitol in a 1:1 mole ratio, is added in small portions. All the components is stirred at room temperature for 2 hours until complete dissolution of the components. Then water for injection is added to the total volume of 90 liter.

pH is checked and adjusted to 7.4-7.6 by adding of sodium hydroxide in small portions, and then water for injection is added for a volume of 100 l. The solution is filtered trough a sterilizing filter and dispensed into sterile 2 ml or 5 ml containers.

The obtained solution comprises 4.85 mass % of 9-oxoacridine-10-acetic acid, 2.00 mass % of 1-deoxy-1-(ethylamino)-D-glucitol, 2.14 mass % of 1-deoxy-1-(propylamino)-D-glucitol (i.e weight ratio of mixture components is respectively 2.42:1:1.06; mass percentage of the mixture in the preparation is 9.0%), 0.005-0.02% of sodium hydroxide; the rest is water for injection.

EXAMPLE 7

The Preparation of the Medicinal Preparation for Parenteral Use, Comprising as Active Ingredient the Mixture of 9-oxoacridine-10-acetic acid and Two Different 1-alkylamino-1-deoxypolyols 125 g of fine crystalline 9-oxoacridine-10-acetic acid is added to 700 ml of water for injection and then, under intensive stirring, 106 g of the mixture of solubilizers: 1-deoxy-1-(propylamino)-D-glucitol and 1-deoxy-1-(etylamino)-D-glucitol in a 1:2 mole ratio, is added in small portions. All the components are mixed and boiled for 20 minutes using a backflow condenser, then the obtained solution is cooled to room temperature, and then water for injection is added for a volume of 900 ml.

pH is checked and adjusted to 7.4-7.6 by adding of diethylamine in small portions, and then water for injection is added for a volume of 1000 ml. The solution is filtered trough a sterilizing filter and dispensed into sterile 2 ml or 5 ml containers.

The obtained solution comprises 12.5 mass % of 9-oxoacridine-10-acetic acid, 3.7 mass % of 1-deoxy-1-(propylamino)-D-glucitol, 6.9 mass % of 1-deoxy-1-(etylamino)-D-glucitol (i.e weight ratio of mixture components is respectively 3.37:1:1.86; mass percentage of the mixture in the preparation is 23.1%), 0.02-0.06% of diethylamine; the rest is water for injection.

EXAMPLE 8

The Preparation of the Medicinal Preparation for Parenteral Use, Comprising as Active Ingredient the Mixture of the Salt (Formed by 9-oxoacridine-10-acetic acid and 1-alkylamino-1-deoxypolyol) and 1-alkylamino-1-deoxypolyol 22.8 g of N-(1-deoxy-L-galactitol-1-yl)-N-ethyl ammonium 9-oxoacridine-10-ylacetate is dissolved in 70 ml of water for injection under intensive stirring. Then water for injection is added to the total volume of 90 ml.

pH is checked and adjusted to 7.4-7.6 by additional adding of 1-deoxy-1-(ethylamino)-L-galactitol in small portions, and then water for injection is added for a volume of 100 ml. The solution is filtered trough a sterilizing filter and dispensed into sterile 2 ml or 5 ml containers.

The obtained solution comprises 22.8 mass % of N-(1-deoxy-L-galactitol-1-yl)-N-ethyl ammonium 9-oxoacridine-10-ylacetate and from 0.4 to 0.11 mass % of 1-deoxy-1-(etylamino)-L-galactitol (i.e weight ratio of mixture components is respectively from 57:1 to 207:1; mass percentage of the mixture in the preparation is from 22.9 to 23.2); the rest is water for injection.

EXAMPLE 9

The Preparation of the Medicinal Preparation for Parenteral Use, Comprising as Active Ingredient the Mixture of N-(1-deoxy-D-glucitol-1-yl)-N-ethyl ammonium 9-oxoacridine-10-ylacetate and 1-deoxy-1-(ethylamino)-D-glucitol 228 g of N-(1-deoxy-D-glucitol-1-yl)-N-ethyl ammonium 9-oxoacridine-10-ylacetate is dissolved in 700 ml of water for injection under intensive stirring. Then water for injection is added to the total volume of 900 ml.

pH is checked and adjusted to 7.4-7.6 by adding of 1-deoxy-1-(ethylamino)-D-glucitol in small portions, and then water for injection is added for a volume of 1000 ml. The solution is filtered trough a sterilizing filter and dispensed into sterile 2 ml or 5 ml containers.

The obtained solution comprises 22.8 mass % of N-(1-deoxy-D-glucitol-1-yl)-N-ethyl ammonium 9-oxoacridine-10-ylacetate and from 0.4 to 0.11 mass % of 1-deoxy-1-(etylamino)-D-glucitol (i.e weight ratio of mixture components is respectively from 57:1 to 207:1; mass percentage of the mixture in the preparation is from 22.9 to 23.2); the rest is water for injection.

EXAMPLE 10

The Preparation of the Medicinal Preparation for Topical Use, Comprising as Active Ingredient the Mixture of 9-oxoacridine-10-acetic acid and 1-alkylamino-1-deoxypolyol 8.8 g of 1-deoxy-1-(propylamino)-L-mannitol and 10.0 g of 9-oxoacridine-10-acetic acid are mixed, the mixture is pounded in a mortar or in a homogenizer; then 50 ml of water, 130 g medicinal Vaseline, 0.2 g of Tween 20 are added; then as preservative sodium benzoate is added; all the components are emulsified in high-speed mixer to provide the homogenous cream.

The obtained cream, comprising 5 mass % of 9-oxoacridine-10-acetic acid and 4.4 mass % of 1-deoxy-1-(propylamino)-L-mannitol, is packaged to cans or tubes.

EXAMPLE 11

The Preparation of the Medicinal Preparation for Topical Use, Comprising as Active Ingredient the Salt of 9-oxoacridine-10-acetic acid and 1-alkylamino-1-deoxypolyol 9.1 g of N-(1-deoxy-D-glucitol-1-yl)-N-ethyl ammonium 9-oxoacridine-10-ylacetate and 89.9 g of 1,2-propyleneglycol is mixed and as preservative methylparaben is added up to 0.15%.

The obtained liquid liniment comprising 9.1 g (9.1 mass %) of N-(1-deoxy-D-glucitol-1-yl)-N-ethyl ammonium 9-oxoacridine-10-ylacetate (it is correspond 5 mass % of 9-oxoacridine-10-acetic acid), is packaged to vials of 5-10 ml volume, and sealed sterilely by ribbon cork and then by aluminum cap.

EXAMPLE 12

The Preparation of the Medicinal Preparation for Oral Use, Comprising as Active Ingredient the Mixture of the Salt (formed by 9-oxoacridine-10-acetic acid and 1-alkylamino-1-deoxypolyol) and 1-alkylamino-1-deoxypolyol 278 g of N-(1-deoxy-L-glucitol-1-yl)-N-ethyl ammonium 9-oxoacridine-10-ylacetate and 32.6, 1-deoxy-1-(ethylamino)-D-glucitol are mixed and granulated in a granulator, adding methylcellulose solution. After sifting, the granulate is dusted with magnesium stearate; and obtained mass is tableted to provide 970 tablet cores.

The surfaces of obtained tablet cores are coated by emulsion composed of 13 mass % of methacrylate and ethacrylate copolymer and 7 mass % of 1,2-propyleneglycol.

As a result of this, the tablets each comprising 0.28 g of N-(1-deoxy-L-glucitol-1-yl)-N-ethyl ammonium 9-oxoacridine-10-ylacetate, 0.03 g of 1-deoxy-1-(ethylamino)-D-glucitol (i.e weight ratio of mixture components is respectively 933:1) and 0,004 g of methylcellulose and magnesium stearate (in total) and 0,015-0,020 g of enteric film coat, are obtained.

EXAMPLE 13

The Preparation of the Medicinal Preparation for Oral Use, Comprising as Active Ingredient the Mixture of 9-oxoacridine-10-acetic acid and 1-alkylamino-1-deoxypolyol 150 g of 9-oxoacridine-10-acetic acid and 160 g of 1-deoxy-1-(ethylamino)-D-glucitol (i.e weight ratio of mixture components is respectively 1:1.07) are mixed and granulated in a granulator, adding methylcellulose solution.

After sifting, the granulate is dusted with magnesium stearate, and obtained mass is tableted to provide 970 tablet cores. The surfaces of obtained tablet cores are coated by emulsion composed of 13 mass % of methacrylate and ethacrylate copolymer and 7 mass % of 1,2-propyleneglycol. The enteric film coat weight is 0,015-0,020 g for each core.

As a result of this, the tablets each comprising 0.15 g of 9-oxoacridine-10-acetic acid, 0.16 g of 1-deoxy-1-(ethylamino)-D-glucitol (i.e the weight fraction of the mixture is more than 99.9% of total mass of the medicinal preparation; weight ratio of the mixture components is respectively 1:1.07), methylcellulose and magnesium stearate amounting to 0,004 g, and 0,015-0,020 g of enteric film coat, are obtained.

EXAMPLE 14

The Preparation of the Medicinal Preparation for Oral Use, Comprising as Active Ingredient the Mixture of the Salt (Formed by 9-oxoacridine-10-acetic acid and 1-alkylamino-1-deoxypolyol) and 1-alkylamino-1-deoxypolyol 278 g of N-(1-deoxy-L-glucitol-1-yl)-N-ethyl ammonium 9-oxoacridine-10-ylacetate and 32.6, 1-deoxy-1-(ethylamino)-D-glucitol are mixed and granulated in a granulator, adding methylcellulose solution (the weight ratio of the mixture components is respectively 8.52:1). After sifting, the granulate is dusted with magnesium stearate, and obtained mass is tableted to provide 970 tablet cores.

The surfaces of obtained tablet cores are coated by emulsion composed of 13 mass % of methacrylate and ethacrylate copolymer and 7 mass % of 1,2-propyleneglycol The enteric film coat weight is 0,015-0,020 g for each core.

As a result of this, the tablets each comprising 0.28 g of N-(1-deoxy-L-glucitol-1-yl)-N-ethyl ammonium 9-oxoacridine-10-ylacetate, 0.03 g of 1-deoxy-1-(ethylamino)-D-glucitol (i.e the weight fraction of the mixture is more than 99.9% of total mass of the medicinal preparation), methylcellulose and magnesium stearate amounting to 0,004 g, and 0,015-0,020 g of enteric film coat, are obtained.

EXAMPLE 15

The Preparation of the Medicinal Preparation for Oral Use, Comprising as Active Ingredient the Mixture of the Different Salts (Formed by 9-oxoacridine-10-acetic acid and 1-alkylamino-1-deoxypolyols) and 1-alkylamino-1-deoxypolyol 134.4 g of N-(1-deoxy-L-mannitol-1-yl)-N-propyl ammonium 9-oxoacridine-10-ylacetate, 147.7 g of N-(1-deoxy-D-galactitol-1-yl)-N-butyl ammonium 9-oxoacridine-10-ylacetate, and 32.6 of 1-deoxy-1-(ethylamino)-D-glucitol are mixed (thus, the weight ratio of the mixture components is respectively 4.38:4.5:1) and granulated in a granulator, adding methylcellulose solution. After sifting, the granulate is dusted with magnesium stearate, and obtained mass is tableted to provide 970 tablet cores.

The surfaces of obtained tablet cores are coated by emulsion composed of 13 mass % of methacrylate and ethacrylate copolymer and 7 mass % of 1,2-propyleneglycol. The enteric film coat weight is 0,015-0,020 g for each core.

As a result of this, the tablets each comprising 0.14 g of N-(1-deoxy-L-mannitol-1-yl)-N-propyl ammonium 9-oxoacridine-10-ylacetate, 0.15 g of N-(1-deoxy-D-galactitol-1-yl)-N-butyl ammonium 9-oxoacridine-10-ylacetate, and 0.03 g of 1-deoxy-1-(ethylamino)-D-glucitol (i.e the weight fraction of the mixture is more than 99.9% of total mass of the medicinal preparation), methylcellulose and magnesium stearate amounting to 0,004 g, and 0,015-0,020 g of enteric film coat, are obtained.

EXAMPLE 16

The Preparation of the Medicinal Preparation for Oral Use, Comprising as Active Ingredient the Mixture of the Salt (Formed by 9-oxoacridine-10-acetic acid and 1-alkylamino-1-deoxypolyols), 9-oxoacridine-10-acetic acid and 1-alkylamino-1-deoxypolyol 198 g of N-(1-deoxy-L-mannitol-1-yl)-N-propyl ammonium 9-oxoacridine-10-ylacetate, 1 g of 9-oxoacridine-10-acetic acid, 1 g of 1-deoxy-1-(ethylamino)-D-glucitol are mixed (thus, the weight ratio of the mixture components is respectively 198:1:1) and granulated in a granulator, adding methylcellulose solution.

After sifting, the granulate is dusted with magnesium stearate, mixed with 800 g of lactose, stirred and encapsulated as 0.5 g into each capsule.

As a result of this, the capsules are obtained and each capsule contains 0.1 g of active ingredient (i.e., the weight fraction of the mixture is approximately 20.0% of total mass of the medicinal preparation), approximately 0.4 g of lactose, and methylcellulose and magnesium stearate amounting to 0,004 g

EXAMPLE 17

The Preparation of the Medicinal Preparation as the Suppository for Rectal or Intravaginal Use, Comprising as Active Ingredient the Mixture of 9-oxoacridine-10-acetic acid and 1-alkylamino-1-deoxypolyol 25 g of finely crystalline 9-oxoacridine-10-acetic acid and 21 g of 1-deoxy-1-(ethylamino)-D-glucitol are mixed; the obtained mixture is added to 104 g of suppository base Witepsol H15 previously molten at 40° C. The hot prepared composition is homogenized and, then, formed and cooled to produce the torpedo-shaped suppositories, each of 1.5 g weight. The yield is 96-98%.

Thus, the suppositories for intravaginal and rectal use, each of 1.5 g weight, are produced and each of them contains: 0.25 r of 9-oxoacridine-10-acetic acid; 21 g of 1-deoxy-1-(ethylamino)-D-glucitol (i.e., the weight ratio of the mixture components is respectively 1:1.19; the weight fraction of the mixture is 30.6% of total mass of the medicinal preparation); and the rest is suppository base Witepsol H15.

EXAMPLE 18

Penetration/Binding of Claimed Compounds with Different Cell Types

To study the rate of penetration/binding of claimed compounds into human cells, peripheral human blood lymphocytes (PBL), cells from human breast cancer line MD-1, human hepatoma cells HepG-2 were used.

Before the treatment with the claimed salts, with the prototype, and (for comparison) with the 9-oxoacridine-10-acetic acid sodium salt, respectively, MD-1 cells ($10^4$ cells/well) were cultivated in 96 well plate during 48 hours in the complete DMEM medium. HepG-2 cells ($5 \times 10^4$ cells/well) were cultivated during 96 hours in the complete DMEM medium. PBL ($5 \times 10^5$ cells/well) were cultivated during 72 hours in the complete DMEM medium. The compound solution in the complete DMEM medium was introduced into the cultural fluid, to obtain the final concentration of corresponding compound of 1 μM. After 15 minutes of incubation, the cells were washed twice with physiological solution, the fluorescence of penetrated/bound salts on the flatbed fluorescence reader Lambda Fluoro 320 E with excitation wavelength of 254 nm and detection wavelength of 510 nm (determination of 9-oxoacridine-10-acetic acid ion). Experiment results were presented in Table 2. From the table data, it may be seen that the amount of the claimed salts, that penetrate into and/or bind with cell, is 5-7 times higher than of the prototype or of the salt of the 9-oxoacridine-10-acetic acid salt with the alkali element. At that, the amount of the compound inside the cell grows exponentially with the increase of the length of the aliphatic radical-substitute at nitrogen atom of amino group of 1-alkiloamino-1-deoxypolyol. Thus, the claimed compounds penetrate the cells considerably faster and/or fixate the cell structures more tightly, than does the prototype.

EXAMPLE 19

Penetration of Claimed Compounds into Tissues After their Local Application in the Inert Carrier Local application of claimed compounds has shown that reactant penetrates into the tissues faster and deeper than the prototype. The rate and the depth of penetration of claimed compounds after their local application were studied on rats weighing 250-280 g. In the animals, 2 skin areas with the dimensions of 1 on 2 cm were shaved on both sides of the back. On the one area, the claimed drug in the solution of inert carrier—1,2-propylene glycol was applied, and on the other (symmetric) area of the same animal the prototype in the same carrier was applied. For individual animal, the concentrations of the applied prototype and of the claimed preparation were the same (from 1% to 10% in various experiment series). Skin areas with preparations applied were covered with polyethylene film to prevent drying and licking the drug away by the animal. After 2 or 4 hours after application of the preparations, the animals were exterminated with etherization, the rest of applied preparations were immediately thoroughly removed with 96% alcohol swabs. From the center of the area, where the compounds had been applied, a skin fragment with 1 sq. cm surface was excised. The acridine (9-oxoacridine-10-acetic acid) component was extracted by homogenization of excised tissue in chloroform with subsequent centrifugation. The content of 9-oxoacridine-10-acetic acid in supernatant was measured by the high-performance liquid chromatography method. The results of the study were presented in Table 3 The results presented in Table 3 show that the claimed compounds penetrate into skin 2-3 times faster than the prototype does.

EXAMPLE 20

Interferon-Inducing Activity of the Claimed Compounds (in the Mononuclear Culture of Human Peripheral Blood, Enriched with Dendritic Cells)

Interferon-inducing activity of claimed compounds in comparison with the prototype was studied in mononuclear culture of human peripheral blood, enriched with dendritic cells, responsible for type I interferon production. Mononuclear cells of human peripheral blood from 20 various healthy donors (n=20) were separated from the whole donor blood (with EDTA added) by centrifugation in velocity sedimentation gradient in the "ficoll:verografin" system. The cells were washed twice with Hanks solution. The washed mononuclear cells of the human peripheral blood were resuspended in RPMI 1640 medium with addition of HEPES-buffer, sodium pyruvate, L-glutamine and inactivated calf serum. The obtained cells were enriched with dendritic cells by immunomagnetic separation method. For this purpose, the cells were incubated with monoclonal antibodies, that specifically bind with dendritic cells (antibodies are binding with specific for dendritic cells lecithin), and then were collected on the column Miltenyi MS (BDCA-4 Cell Isolation Kit (Miltenyi Biothec) was used). After the enrichment procedure, the portion of interferon-producing (dendritic) cells increased about 20 times. Diluted in the same medium (RPMI 1640, but without serum) cells in concentration of $1.5 \times 10^6$ in 1 ml, were inoculated on 24 well flat-bottomed plates at 1 ml in a well and cultivated in thermostat at 37° C. during 24 hours either with the claimed compounds or with the prototype, or without both of them (control=spontaneous cytokine production). After that, the cells were centrifuged, supernatant was separated and the levels of interferons, in particular, of interferon-gamma, interferon-alpha, interferon-omega, in the supernatant were determined with immune-enzyme (ELISA) analysis. All the claimed compounds (or the prototype) were added to the cultivating medium up to the concentration of 30 micromoles/ml. The results of the study are presented in table No. 7.

isomers of the same compound have various activities regarding the interferon induction. So, for example, the compound 12 (L-isomer) has increased the level of gamma-interferon production more significantly, than its D-isomer analogue (compound 4) did. Regarding the omega-interferon, the relationship in some cases was inverse. The compound 1 (D-isomer) induced larger amount of the omega-interferon, than its L-isomer variant (compound II) did. Thus, the claimed compounds possess much more pronounced interferon-inducing activity, than the prototype, and the spectrum of interferons induced by them has different profile, than the spectrum of interferons induced by the prototype.

EXAMPLE 21

Cytokine-Inducing Activity of Claimed Compounds (in the Mononuclear Culture of Human Peripheral Blood)

Cytokine-inducing activity of claimed compounds in comparison with the prototype was studied in the mononuclear culture of human peripheral blood. The experiments were carried out on mononuclear cells from blood samples of 20 various healthy donors (n=20). Mononuclears from human peripheral blood were separated from the whole donor blood (with EDTA added) by centrifugation in Histopaque 1077 density gradient. Cells were washed twice with Hanks solution. The washed mononuclear cells from human peripheral blood, diluted in the 199 medium in concentration of $1.5 \times 10^6$ in 1 ml, were inoculated on 24 well flat-bottomed plates at 1 ml in a well and cultivated in thermostat at 37° C. during 24 hours either with claimed compounds or with prototype, or without both of them (control=spontaneous cytokine production). After incubation, supernatant was collected and the cytokine level was determined with immune-enzyme analysis (ELISA), in particular, that of interleukin-2 (IL-2), interleukin-4 (IL-4), interleukin-10 (IL-10). In separate experiment series, the ability of the claimed compounds to prevent the induction of the pro-inflammatory cytokine tumor necrosis factor-alpha (TNF-alpha) was studied (in comparison with the prototype), in response to the synthetic oligodeoxynucle- TABLE No. 7

Interferon-inducing activity of claimed compounds (in the mononuclear culture of human peripheral blood, enriched with dendritic cells)*.

| Index* | Proto-type | The claimed compounds (Compound No and radical description R of the substituting group at the nitrogen atom of amino group of the 1-alkiloamine-1-deoxypolyol in parentheses) | | | | | |
|---|---|---|---|---|---|---|---|
| | | 1,(R = ethyl), D-isomer | 11,(R = propyl) L-isomer | 4,(R = propyl) D-isomer | 12,(R = propyl), L-isomer | 2(R = butyl) D-isomer | 15(R = butyl), L-isomer |
| Alpha-Interferon, pg/ml, mean | 22.0/85.7 (3.9) | 23.0/103.5 (4.5) | 19.0/90.4 (4.7) | 27.1/140.9 (5.2) | 21.2/106.0 (5.0) | 16.3/105.1 (6.5) | 19.3/131.2 (6.8) |
| Gamma-interferon, pg/ml, mean | 12.0/50.5 (4.18) | 10.0/85.3 (8.53) | 14.0/161.6 (11.5) | 13.0/158.6 (12.2) | 11.0/169.4 (15.4) | 16.0/243.2 (15.2) | 9.4/160.0 (16.7) |
| Omega-interferon, pg/ml, mean | 24.0/30.3 (1.3) | 23.2/223.2 (9.6) | 18.0/133.2 (7.4) | 25.0/217.5 (8.7) | 17.2/153.1 (8.9) | 23.4/212.9 (9.1) | 28.2/265.1 (9.4) |

*The spontaneous interferon production (in absence of the claimed compounds and the prototype) is in denominator, values of induced interferon levels are in numerator, induction factor is in parentheses.

The data presented in the table show that claimed compounds present greater interferon-inducing activity than the prototype, and the interferon-inducing activity increases with the increase of the length of the aliphatic radical-substitute at the nitrogen atom of amino group of the ion (1-alkylamino-1-deoxypolyol) in series (ethyl, propyl, butyl). Besides, the prototype has not influenced anyhow the omega-interferon production level. Also, it suddenly turned out, that L and D otide CpG-ODN (imitating the cell contact with bacteria). CpG-ODN was introduced into the cultivating medium up to 19 mcg/ml concentration, simultaneously with studied compounds. TNF-alpha was determined in cultural liquid with the ELISA method as well. After 24-hours incubation, all the claimed compounds (or the prototype, correspondingly) were added to the cultivating medium up to 30 μM/ml concentration. The results of the study are presented in Table No. 8

TABLE No. 8

Cytokine-inducing activity of the claimed compounds (in the culture of mononuclear cells from human peripheral blood)

| Index* | Prototype | 1,(R = ethyl), D-isomer | 11,(R = propyl) L-isomer | 4,(R = propyl) D-isomer | 12,(R = propyl) L-isomer | 2(R = butyl) D-isomer | 15(R = butyl) L-isomer |
|---|---|---|---|---|---|---|---|
| Interleukin - 10, pg/ml, mean | 1547 | 2927 | 2121 | 2947 | 2844 | 3220 | 3190 |
| Interleukin - 4, pg/ml, mean | 4320 | 5432 | 5387 | 6480 | 6122 | 7124 | 6980 |
| Interleukin - 2, pg/ml, mean | 242 | 899 | 745 | 1021 | 1211 | 2654 | 2385 |
| TNF - alpha, induced CpG-ODN, pg/ml, mean | 16 | 8 | 9 | 4 | 6 | 4 | 3 |

*Data concerning the induction are normalized by subtraction of value of spontaneous cytokine production level (in the absence of claimed compounds or prototype) from the values of induced cytokines level.

The data presented in the table show that the claimed compounds are showing greater cytokine-inducing activity regarding the single anti-inflammatory interleukins, and the cytokine-inducing activity increases with the increase of the length of the aliphatic radical-substitute at the nitrogen atom (1-alkylamino-1-deoxypolyol group) in series "-ethyl, -propyl, -butyl". The prototype in contrast to the claimed compounds has poorly influenced the CpG-ODN-induced level of tumor necrosis factor-alpha. Also, it suddenly turned out that L and D isomers of the same compound have various activity regarding the induction of certain cytokines. Thus, for example, the compound II (L-isomer) increased the production level of interleukin-10 only by 2112 pg/ml from the spontaneous production, while its D-isomeric variant (compound 1) increased the production level of the same cytokine on 2927 pg/ml. Regarding the interleukin-2, the situation was inverse. Compound II (L-isomer) induced more quantity of interleukin-2, than its D-isomer (compound 1). Thus, the claimed compounds possess much more pronounced cytokine-inducing activity regarding the anti-inflammatory cytokines and greater ability to suppress the synthesis of pro-inflammatory cytokines than the prototype, and the spectrum of cytokines induced by them has a different profile, than that of cytokines induced by the prototype.

EXAMPLE 22

Immunomodulating Activity of the Claimed Compounds

Immunomodulating activity of the claimed compounds was studied in comparison with prototype at single intravenous injection of 0.2 M water solutions to Wistar line rats at dose of $8.0 \times 10^{-4}$ M/kg of body weight. The baseline parameters of immune system and the same after compounds exposure were studied: phagocytic activity of peripheral blood neutrophils, oxygen-dependent metabolism of peripheral blood neutrophils, serum interferon level (in 4 hours), CD4 (+) and CD8 (+) lymphocytes amount (on the $3^{rd}$ day). Neutrophils oxygen-dependent metabolism was determined with luminol-dependent chemiluminescence (ChL) method. ChL intensity measuring was performed on a biochemiluminometer. Neutrophils oxygen-dependent metabolism was estimated as the $I_{summ.}$—total amount of impulses, emitted by $1 \times 10^3$ neutrophils during the HL-response registration time (30 min). The serum interferon level was determined with the biological method (index of cells protection against Sendai virus infection in culture) in comparison with standard interferon preparation, the value was expressed in International Units (IU). The relative amount of CD4 (+) and CD8 (+) lymphocytes was determined by means of monoclonal antibodies using a flow cytometer. Also the change of proliferation response of the whole blood cells culture to the standard mitogen (phytohaemagglutinin) as degree (rate) of change of $[H^3]$-thymidine intake into cells DNA during 1 hour incubation at 37° C. was studied. The results of the study are presented in the Table No. 9.

TABLE No. 9

Immunomodulating activity of the claimed compounds.

| Index* | Prototype | 6 (R = ethyl) | 11 (R = ethyl) | 2 (R = propyl) | 17 (R = propyl) | 13 (R = butyl) | 8 (R = butyl) |
|---|---|---|---|---|---|---|---|
| $I_{summ.}$, imp./$10^3$ neutrophils/30 min., mean | 6034/9645 | 6432/11342 | 6137/11552 | 6118/12590 | 6766/12420 | 6089/13716 | 6282/14023 |
| Serum interferon, $10^3$ IU/ml, mean | 5/320 | 6/450 | 8/480 | 7/720 | 9/750 | 7/970 | 5/950 |
| CD 4 (+) lymphocytes, %, mean | 40/42 | 41/43 | 42/44 | 43/45 | 42/45 | 43/46 | 43/46 |

TABLE No. 9-continued

Immunomodulating activity of the claimed compounds.

| | | The claimed compounds (Compound No and, in parentheses, the description of radical R of the substituting group at the amino group of the cation) | | | | | |
|---|---|---|---|---|---|---|---|
| Index* | Prototype | 6 (R = ethyl) | 11 (R = ethyl) | 2 (R = propyl) | 17 (R = propyl) | 13 (R = butyl) | 8 (R = butyl) |
| CD 8 (+) lymphocytes, %, mean | 35/33 | 33/29 | 34/30 | 35/28 | 34/27 | 33/25 | 34/24 |
| CD 4 (+)/CD 8 (+) ratio | 1.14/1.27 | 1.24/1.48 | 1.24/1.46 | 1.23/1.61 | 1.24/1.67 | 1.30/1.84 | 1.26/1.92 |
| Level of the PhGA-stimulated cell proliferative response | 2.64/3.25 | 2.86/4.48 | 2.73/4.57 | 2.43/5.25 | 2.53/5.64 | 2.45/5.89 | 2.52/5.84 |

*The baseline parameters are in the denominator, the parameters after exposure are in the numerator.

The results clearly suggest that the claimed compounds are significantly more active, than the prototype according to their influence upon all the components of immune system: the induced interferon level is significantly higher, more significant increase of the T-helpers/T-suppressors ratio occurs, as well as that of the proliferative response of the white blood cells to mitogen. Besides, a positive correlation is determined between the response intensity of the immunity indices and the length of the aliphatic radical-substitute at the nitrogen atom of the 1-alkylamino-1-deoxypolyol amino group.

EXAMPLE 23

The Direct Antiviral Activity of the Claimed Compounds (Against Different Viruses in Cell Cultures)

Antiviral activity of the claimed compounds in comparison with the prototype was studied in different in vitro systems (Table No. 10). The claimed compounds or the prototype, correspondingly, were introduced into the corresponding culture on the $2^{nd}$-$7^{th}$ day after viral contamination of the culture. All the compared compounds were introduced into the culturing medium in separate experiments with appointed virus in equimolar quantities.

TABLE No. 10

Antiviral activity of the claimed compounds

| | | | Difference in titers of the corresponding virus in the preparation's presence and without it (negative control of the preparation), lg TCID50* | | | | | | |
|---|---|---|---|---|---|---|---|---|---|
| | | | | The claimed compounds (Compound's number and R substitute radical name at cation aminogroup) | | | | | |
| Virus/ nucleic acid's type | Presence of capsid | Cell culture for virus titration | The prototype | 1 ethyl | 11 ethyl | 4 propyl | 7 propy | 2 butyl | 15 butyl |
| Carnivores distemper virus/RNA | + | Cell culture 4647 | 1.1 | 2.23 | 2.28 | 2.35 | 2.41 | 2.55 | 2.62 |
| Aujeszky's disease virus/DNA | + | Primary culture of chicken fibroblasts | 1.1 | 1.62 | 1.66 | 1.69 | 1.72 | 1.78 | 1.78 |
| Bovine Viral Diarrhea Virus/RNA | + | Calf coronary vessel cell culture | 0.9 | 1.52 | 1.54 | 1.58 | 1.60 | 1.67 | 1.69 |
| Infectious bovine rhinotracheitis virus/DNA | + | Taurus-1 strain cells | 1.7 | 2.26 | 2.28 | 2.27 | 2.27 | 2.35 | 2.41 |
| Adenovirus type 1/DNA | − | Taurus-1 strain cells | 0.1 | 1.72 | 1.71 | 1.82 | 1.83 | 1.86 | 1.89 |
| Parvovirus/ DNA | − | Cells of strain FS | 0.1 | 1.56 | 1.63 | 1.65 | 1.72 | 1.74 | 0 |
| Human hepatitis C virus of 1b genotype/RNA | + | Vero cells | 2.0 | 2.8 | 3.0 | 3.1 | 3.1 | 3.3 | 3.3 |

*TCID 50 - a viral dose that killed 50% of the cultured cells.

The data presented in the table No. 10 show that unlike the prototype, the claimed compounds possess higher efficacy, as well as different antiviral activity spectrum; in particular, it follows particularly from the fact that they (unlike the prototype) much more significantly affect non-enveloped viruses. At that, an increase in antiviral activity in the series of the claimed salts at the length increase of the aliphatic radical-substitute at the nitrogen atom of the 1-alkylamino-1-deoxy-polyol ion's amino group is noted.

EXAMPLE 24

Antimicrobial Activity of the Claimed Compounds (on the Experimental Model of Bacterial Sepsis)

Outbred white mice with body weight 23-25 g were used in the experiment. All the mice groups (10 mice in each group) were injected intravenously in the retroorbital sinus with bacteria of *Staphylococcus aureus* VT-2003R pathogenic strain at a dose of $1 \times 10^{10}$ bacterial cells per mouse. Two hours after contamination, the products to be investigated were injected intravenously once. The groups from 1 to 6 were administered with the claimed compounds (Nos. 1, 5, 9, 2 as well as their mixtures), the $7^{th}$ group was administered with the prototype, the $8^{th}$ group was administered with the vehicle (water for injection), as a negative control group. The claimed compounds (or their mixtures) and the prototype were injected in equal dose of 6 mg (calculated as the residue of 9-oxoacridin-10-acetic acid) per kilogram body weight of the animal. The overall survival rate of the animals during 32 hours after the contamination was assessed. The results of the experiment are presented in Table No. 11.

TABLE No. 11

Antimicrobial activity of the claimed compounds (on the experimental model of bacterial sepsis).

| Group* | Mice survival rate for different periods of time after *Staphylococcus aureus* contamination, % | | | | | | | | |
|---|---|---|---|---|---|---|---|---|---|
|  | 0 h. | 2 h. | 4 h. | 6 h. | 8 h. | 12 h. | 24 h. | 28 h. | 32 h. |
| 1 - (Claimed compound 1) (R = ethyl) | 100 | 100 | 100 | 80 | 70 | 60 | 60 | 50 | 40 |
| 2 - (Claimed compound 5) (R = propyl) | 100 | 100 | 100 | 90 | 80 | 70 | 70 | 60 | 50 |
| 3 - (Claimed compound 9) (R = ethyl) | 100 | 100 | 100 | 80 | 70 | 60 | 60 | 50 | 40 |
| 4 - (Claimed compound 2) (R = butyl) | 100 | 100 | 100 | 100 | 90 | 80 | 70 | 70 | 60 |
| 5- (Mixture of claimed compounds 1 and 5) | 100 | 100 | 100 | 90 | 90 | 80 | 80 | 70 | 70 |
| 6 - (Mixture of claimed compounds 2 and 9) | 100 | 100 | 100 | 90 | 90 | 80 | 80 | 70 | 70 |
| 7 - (prototype) | 100 | 100 | 70 | 70 | 50 | 40 | 30 | 20 | 20 |
| 8 - (negative control) | 100 | 100 | 70 | 50 | 40 | 30 | 20 | 10 | 10 |

*All the claimed compounds (or their mixture - groups 5 and 6) and the prototype were injected in equimolar quantities, the molar ratio of claimed compounds in mixtures (groups 5 and 6) was 1:1.

The data presented in the table No. 11 show that claimed compounds and their mixtures have much more significant antimicrobial activity than the prototype. At that, an increase in antimicrobial activity in the series of claimed salts at the length increase of the aliphatic radical-substitute at the nitrogen atom of the 1-alkylamino-1-deoxypolyol ion's amino group is noted. Besides, some of the mixtures of the claimed salts possess rather more efficacy, than the same salts alone.

EXAMPLE 25

Antifungal Activity of the Claimed Compounds (on the Experimental Fungal Sepsis Model)

To outbred white mice (10 animals in each group) were injected intravenously with $LD_{50}$. dose of suspension of *Candida Albicans* fungi culture, obtained by sub-cultivating of pathogenic clinical isolate. On the $3^{rd}$ day after contamination, the mice were injected intravenously with the compounds to be compared. The groups from 1 to 6 received the claimed compounds (compounds Nos. 6, 7, 8, 13 as well as their mixtures at different molar ratio), the $7^{th}$ group received the prototype, the $8^{th}$ group received the vehicle (water for injection), as a negative control group. The prototype and the claimed compounds (or the mixtures of the claimed compounds) were injected in equal dose 6 mg (calculated as 9-oxoacridin-10-acetic acid residue) pre kilogram body weight of the animal. The overall survival rate of the animals during 7 days after the contamination was assessed. The results of the experiment are presented in Table No. 12.

TABLE 12

Antifungal activity of the claimed compounds (on the experimental fungal sepsis model).

| Group* | Mice survival rate at different terms after *Candida albicans* contamination, % | | | |
|---|---|---|---|---|
|  | $1^{st}$ day | $3^{rd}$ day | $5^{th}$ day | $7^{th}$ day |
| 1 - (Claimed compound 6) | 100 | 90 | 80 | 60 |
| 2 - (Claimed compound 7) | 100 | 90 | 90 | 70 |
| 3 - (Claimed compound 8) | 100 | 90 | 90 | 80 |
| 4 - (Claimed compound 13) | 100 | 90 | 80 | 80 |
| 5 - (Mixture of claimed compounds 6 and 7; 1:1) | 100 | 90 | 90 | 90 |
| 6 - (Mixture of claimed compounds 8 and 13; 1:4) | 100 | 100 | 100 | 100 |
| 7 - (prototype) | 100 | 70 | 50 | 50 |
| 8 - (negative control) | 100 | 80 | 50 | 50 |

*All the claimed compounds (or their mixture - groups 5 and 6) and the prototype were injected in equimolar quantities, the molar ratios of claimed compounds in mixtures (groups 5 and 6) were 1:1 and 1:4, respectively.

The data presented in the table No. 12 show that claimed compounds have much more significant antifungal activity immediately after completion of the treatment. The results are presented in Table No. 13.

TABLE 13

Antitumor activity of the claimed compounds (in combined treatment of an experimental tumor).

| Group/substances | Animal body weight, g. | | Tumor weight, g. | Index of tumor inhibition., % | Survival at day 22 | |
|---|---|---|---|---|---|---|
| | | | | | Living | Dead |
| Cyclophosphan and compound 6 (R = ethyl) | Before After | 23.4 21.2 | 2.48 | 65.98 | 17 | 3 |
| Cyclophosphan and compound 7 (R = propyl) | Before After | 23.5 20.4 | 2.10 | 71.19 | 15 | 5 |
| Cyclophosphan and compound 8 (R = butyl) | Before After | 24.2 19.8 | 1.75 | 76.00 | 16 | 4 |
| Cyclophosphan and the prototype | Before After | 23.7 15.4 | 4.82 | 33.88 | 10 | 10 |
| Negative control (water for injection) | Before After | 21.2 17.1 | 7.29 | — | 18 | 2 | than the prototype. At that, an increase in antifungal activity in the series of claimed salts at the length increase of the alkyl radical substitutent at the nitrogen atom of amino group of 1-alkylamino-1-deoxypolyol cation (in the series "-ethyl; -propyl; -butyl") is noted. Besides, some claimed salts mixtures possess rather more protective effect, than the same salts alone.

EXAMPLE 26

Antitumor Activity of the Claimed Compounds (at Combined Treatment Of an Experimental Tumor)

The studies were carried out using 60 BALB/C line mice with body weight of 20-25 g. Strain ACATON (intestinal adenocarcinoma) was inoculated in the left side of the animals. On the $7^{th}$ day after inoculation, the animals were divided into 3 groups, of 20 mice in each. First group received intraperitoneally the claimed compounds, dissolved in the water for injection in dose of 10 mg/kg of body weight (calculated as 9-oxoacridin-10-acetic acid residue), every second day, beginning on the $7^{th}$ day after tumor inoculation, 7 injections in total; $2^{nd}$ group received the prototype in the same (equimolar) dose, the solvent and the route of administration were the same. Additionally all the animals were injected with cytostatic agent cyclophosphan in dose of 7 mg per kg of body weight intraperitoneally daily for 10 days. $3^{rd}$ group served as negative controls and received the vehicle (water for injection), 0.4 ml per mouse intraperitoneally daily for 10 days as well. All the animals were euthanized on day 22 after tumor inoculation. The tumors were excised and average tumor weight was determined in each animal group. Antitumor activity of the preparations was determined as the index of tumor growth inhibition. The growth inhibition index in each group was calculated by a formula:

$$II (\%) = \frac{\text{Average tumor weight in the negative control group} - \text{average tumor weight in the group}}{\text{Average tumor weight in the negative control group}}$$

To estimate the toxicity, the animal's body weight was recorded before the substances administration onset and The data presented in the table No. 13 show that the claimed compounds possess much more significant antitumor activity than the prototype, and toxic effects in groups received the claimed compounds (body weight loss) are lower. Animal survival rate in groups receiving the claimed compounds was significantly higher than in the group receiving the prototype. At that, it was noted that antitumor activity in the series of claimed salts increase parallel to the length increase of the aliphatic radical-substitute at nitrogen atom of amino group of a cation (1-alkylamino-1-desoxypolyol).

EXAMPLE 27

Antiparasitic Activity of the Claimed Compounds (in the Experimental Opistorchosis Model)

The experiment was performed on on 60 gold hamsters (males, 100 g of body weight) infested per os by 50 metacercariae of O. felineus. Starting the second day after infestation, during two weeks, the claimed compounds were administered intramuscularly at a dose of 4 mg/kg of body weight (calculated as 9-oxoacridin-10-acetic acid residue) every third day or, accordingly, the prototype was administered at the same dose. (All the substances were injected intramuscularly, dissolved in the water for injection (0.5 ml per animal). Animals with untreated opistorchosis infection served as negative control (they received the vehicle only i.e water for injection was injected in the same volume), and intact healthy gold hamsters served as intact control. Functional activity of peripheral blood neutrophils was determined according to their capacity to engulf latex particles of 2.7 mkm diameter (Hamburger's index i.e. the percentage of active cells, Wright index i.e. average of engulfed particles per one phagocytic cell). Indices of O. felineus metacercariae level infestation were a number of eggs in one gram of animal excrements and a number of opisthorchis maritaes in liver that was examined after gold hamsters' euthanasia. The results of the study are presented in Table No. 14.

TABLE No. 14

Antiparasitic activity of the claimed compounds
(on the experimental opistorchosis model).

| | Observed animal groups | | | | |
|---|---|---|---|---|---|
| Indices | Intact animals | Negative control (water for injection) | The prototype | Claimed compound 1 | Claimed compound 2 |
| Percentage of suppression of metacercariae infestation | — | 0% | 44%: | 100% | 100% |
| Egg production intensity, egg/g of excrements | — | 26.8 | 21.4 | 4.8 | 5.4 |
| Hamburger's index | 31.45 | 19.23 | 15.75 | 32.71 | 30.11 |
| Wright index | 2.94 | 1.89 | 2.12 | 3.29 | 3.36 |

The data presented in the table show that the claimed compounds possess significantly greater influence on leucocyte and peripheral blood phagocytic activity and completely suppress the metacercariae infestation, and, thus, possess significantly higher antiparasitic efficacy, than the prototype.

EXAMPLE 28

Antiphlogistic Activity of the Claimed Compound (in the Suppression of The Inflammatory Granulation, Caused by the Subcutaneous Implantation of Cotton Pellets)

Randomly bred Sprague-Dowley rats weighing 160-220 g were used were used. Under ketamine anesthesia (60 mg/kg intraperitoneally), rats were implanted s.c. in the inguinal region with two cotton pellets of 30 mg weight each. The claimed compounds or the prototype, relatively, were injected in water solution at dose of 20 microMol/kg animal body weight (that is 5 mg/kg, calculated as 9-oxoacridin-10-acetic acid residue) on the $1^{st}$, $2^{nd}$, $5^{th}$, $8^{th}$ day after implantation. The control group received the vehicle (water for injection) in 0.25 ml volume by the same regimen. On the $9^{th}$ day, the animals were euthanized with ethyl ether, the cotton pellets along with the surrounding granuloma were dissected out and dried at 60° C. during 24 hours, and then weighted. Antiphlogistic activity was determined according to the capacity of the claimed compound or the prototype to decrease the mass of the granulation tissue and of the inflammatory infiltration, in comparison with those of the control group. The data are presented in the Table No. 15.

TABLE 15

Antiphlogistic activity of the claimed compound (on the suppression of
the inflammation in the "cotton pellet granuloma" test).

| Compounds | Claimed compound No and (in parenthesis) radical meaning R of the substituting group at the nitrogen atom of aminogroup of the 1-alkylamino-1-desoxypoliol ion. | Number of animals in the group | Pellet weight (mg), mean | Inflammation suppression percentage (%) |
|---|---|---|---|---|
| Control (water for injection) | | 6 | 87 | — |
| The prototype | | 6 | 76 | 12.7 |
| The claimed compounds | 1 (R = ethyl) | 6 | 65 | 25.3 |
| | 6 (R = ethyl | 6 | 63 | 27.6 |
| | 4 (R = propyl) | 6 | 52 | 40.3 |
| | 7 (R = propyl) | 6 | 54 | 38.0 |
| | 3 (R = butyl) | 6 | 48 | 44.9 |
| | 15 (R = butyl) | 6 | 46 | 47.2 |

The data presented in the table show that the claimed compounds possess a significantly higher antiphlogistic and antisclerotic activity, than the prototype.

EXAMPLE 29

Radioprotective and Stressprotective Activities of the Claimed Compounds (on the Model of Acute Radiation Syndrome, Caused by Total Irradiation)

Male Wistar's rats weighing 210-230 g were used. Animals were randomized into 6 groups with 20 animals in each group. Water solutions of the claimed compounds (group 1, 2, 3) or of the prototype (group 4) were administered in the stomach of the animals with pump at a dose 1 mMol/kg body weight. The volume of solution was 0.2 ml per 100 g of animal weight. The negative control group of animal (Group 5 was considered negative control group) has received intragastrically same volume of bi-distilled water, another group (Group 6 was considered intact control group) has received distillated water of the same volume as well. Total irradiation was performed with the X-ray unit RUM-17 at the dose 6.5 Gy in 4 hours after injection of preparations. All animals groups were subjected to irradiation, except the group of intact controls. At 24 hours after irradiation, the half of each group of animals was weighted, decapitated and simultaneously the arterial blood, thymus, spleen and adrenal gland sampling was performed to assess the stressprotective activity of compounds. Stressprotective activity of the claimed compounds and of the prototype was assessed by the dynamics of change of relative (relatively to the body weight) weights of spleen, thymus and adrenal glands and blood serum cortisol level to blood serum insulin level ratio (on the $1^{st}$ day after irradiation). To estimate the radioprotective activity of compounds another half of each group was decapitated on the $7^{th}$ day after irradiation. Radioprotective activity was assessed on the basis of the dynamics of change in white blood indices: absolute leukocyte number, relative amount of leukocytes and hemoglobin level (to the $7^{th}$ day). The results of the study are presented in Table No. 16.

The data presented in the table show that the claimed compounds protect the organism much more efficiently than the prototype from the irradiation both regarding the stress alteration (involution of lymphoid tissue and hormonal changes) and regarding the damaging action of radiation on the blood cells and/or their production. At that, there are the positive correlation between the length of aliphatic radical at the nitrogen atom of the cation (1-alkylamino-1 deoxypoliol) in the series of the claimed compounds and the stressprotective/radioprotective activity level. Thus, the claimed compounds possess more significant radioprotective and stressprotective activities, than the prototype.

EXAMPLE 30

Immunomodulating Activity of Claimed Medicinal Preparation (in Treatment of Immunodeficiency in Patients with Severe Burn Injury)

Immunomodulating properties of the claimed medicinal preparation in clinical trials are studied in treatment of secondary immunodeficiency, caused by severe burn.

A group of 54 patients aged 28-43 years (23 female and 31 male) suffered the burn disease with severe grade of burn injury (the affected area consisted 22%-38% of body surface, Frank index was from 73 to 126 units) was under observation. The treatment of patients either with the claimed medicinal preparation (Group 1) or with prototype (Group 2) was performed on the basis of traditional intensive care (for example, infusion and transfusion therapy, antibacterial therapy, preparations improving microcirculation and blood rheology, parenteral and enteral nutrition, enterosorption, necrotomy and autodermoplasty surgeries); at that the patients were randomly assigned into 2 groups. Patients of both groups were comparable regarding sex, age and burn injury severity, regimen and schedule of performed conventional therapy. Starting from day 4 after injury, the preparations were injected intravenously as a bolus injection once a day at dose of 250-500 mg (calculated as 9-oxyacridine-10-acetic acid) according the treatment course on the $1^{st}$, $2^{nd}$, $4^{th}$, $6^{th}$, $8^{th}$, TABLE No. 16

Radioprotective and stressprotective activities of the claimed compounds (in the model of acute radiation syndrome, caused by total irradiation).

| Group No, compound No and the meaning of the R radical at the nitrogen atom of the aminogroup of the 1-alkylamino-1-desoxypoliol ion for the claimed compounds. | Relative weight (mg/100 g body weight) on the $1^{st}$ day after irradiation | | | Hormonal changes on the $1^{st}$ day after irradiation Cortisol/insulin ratio in serum, mean | Blood indices on the $7^{th}$ day after irradiation | | |
|---|---|---|---|---|---|---|---|
| | Thymus | Spleen | Adrenal glands | | Blood hemoglobin, g/l, mean | Leukocytes, $10^9$/l, mean | Lymphocytes, %, mean |
| Group 1, claimed compound 1 | -ethyl | 116 | 432 | 17.0 | 2.9 | 126.4 | 7.23 | 50.32 |
| Group 2, claimed compound 2 | -propyl | 118 | 476 | 16.9 | 3.2 | 132.1 | 7.52 | 52.14 |
| Group 3, claimed compound 3 | -butyl | 122 | 495 | 17.2 | 3.4 | 135.2 | 8.24 | 54.03 |
| Group 4, prototype | — | 92 | 397 | 16.5 | 2.3 | 112.1 | 5.02 | 38.24 |
| Group 5, negative control | — | 85 | 335 | 15.4 | 1.75 | 108.3 | 3.82 | 35.34 |
| Intact control | — | 123 | 552 | 18.5 | 4.29 | 152.1 | 12.34 | 74.30 |

$11^{th}$, $14^{th}$, $17^{th}$, $20^{th}$, $23^{rd}$, $26^{th}$ day. Absolute and relative amount of T-helper lymphocytes (Th), T-suppressor lymphocytes (Ts) and their ratio (Th/Ts) were estimated. The degree of changes of said indices as compared to the normal ones (mean indices of healthy blood donors) were calculated. Immune status examination was carried out on the $3^{rd}$ day after injury (before the initiation of treatment with the claimed medicinal preparation or with the prototype) and on the next day after completion of course of treatment with preparations. The data are presented in Table No. 17.

The first group received basic antibacterial therapy (BAT): ofloxacin in 200 mg 2 times a day during 15 days. To the second group, in addition to BAT, the claimed medicinal preparation in single dose of 250 mg (calculated as 9-oxoacridine-10-acetic acid) was administered; the third group, in addition to BAT, received the prototype in single (=daily) dose of 250 mg (calculated as 9-oxoacridine-10-acetic acid). Both preparations were injected intramuscularly on the $1^{st}$, $2^{nd}$, $4^{th}$, $6^{th}$, $8^{th}$, $11^{th}$, $14^{th}$, $17^{th}$, $20^{th}$, $23^{rd}$ day of the treatment course (10 injections in total). Efficacy of the therapy was TABLE No. 17

Immunomodulating activity of claimed medicinal preparation (in treatment of immunodeficiency in patients with severe burn injury).

| | Group of patients, receiving | | | | | |
|---|---|---|---|---|---|---|
| | Conventional therapy | | Conventional therapy and the claimed medicinal preparation | | Conventional therapy and the prototype | |
| Index | | | | | | |
| Number of patients in group | 18 | | 18 | | 18 | |
| Period after injury | $3^{rd}$ day | $30^{th}$ day | Before the course ($3^{rd}$ day) | After the course ($30^{th}$ day) | Before the course ($3^{rd}$ day) | After the course ($30^{th}$ day) |
| Th, % of the norm, mean | 31 | 40 | 32 | 57 | 34 | 45 |
| Th/Ts, % of the norm, mean | 18 | 31 | 22 | 83 | 20 | 44 |
| % of the adverse events (allergic reactions, caused by the preparation) | — | — | — | 0% | — | 11% |

The data presented in the table show that the claimed medicinal preparation possess higher efficacy, than the prototype, with lower rate of adverse events.

EXAMPLE 31

Antibacterial (Anti-Chlamydia) and Immunomodulating (Immuocorrecting) Efficacy of the Claimed Medicinal Preparation (in Women with Chronic Inflammatory Diseases Of Uterus and Appendages Caused by *Chlamydia*)

The study of anti-Chlamydia and immunomodulating activity of the claimed medicinal preparation was performed in women with chronic inflammatory diseases of uterus and appendages caused by *Chlamydia*. Diagnosis was verified with polymerase chain reaction (PCR). All the women (45 persons) were randomized in 3 groups, 15 persons in each. The first group received basic antibacterial therapy (BAT): assessed on the basis of the disease duration, dynamics of clinical and laboratory indices, disease relapse rate. In all patients laboratory recovery control test after the treatment completion was performed with polymerase chain reaction (PCR). The first control test was performed immediately after the treatment completion, and the final control test (aetiological recovery control test) was performed to the end of the second month after the treatment completion. Besides, the immunological indices were studies, taking into account the immunodeficiency, naturally accompanying *Chlamydia* infection. The mean polymorphonuclear leucocyte (PNL) cytoplasmic granules amount was also assessed as an integral index of antibacterial phagocytic activity of the cell-component of the immune system, directly reflecting their ability to digest the engulfed Chlamydiae. The data related to treatment efficacy in three groups of patients are presented in Table No. 18.

TABLE No. 18

Antibacterial (anti-*Chlamydia*) and immunomodulating (immuocorrecting) efficacy of the claimed medicinal preparation (in females with chronic inflammatory diseases of uterine appendages of the *Chlamydia* aetiology).

| | | Group of patient, receiving | | | | | |
|---|---|---|---|---|---|---|---|
| | | Basic antibacterial therapy, BAT (N = 15) | | BAT and the claimed medicinal preparation (N = 15) | | BAT and the prototype (N = 15) | |
| Index: | | | | | | | |
| Etiological recovery, % | | 69 | | 98 | | 76 | |
| Immune system indices: | Control (healthy donors) (N = 10) | Before treatment | After treatment | Before treatment | After treatment | Before treatment | After treatment |
| Amount of cytoplasmic granules in peripheral blood PNLs, mean | 15 | 8.5 | 10.2 | 9.0 | 14.3 | 9.3 | 11.5 |
| Serum interferon, $\log_2$ IU/ml, mean | 2.6 | 0.2 | 0.8 | 0.2 | 2.5 | 0.3 | 1.2 |
| Alpha-interferon, produced by the peripheral blood leukocytes, and induced in culture by the Newcastle disease virus, $\log_2$ IU/ml, mean | 9.4 | 5.1 | 5.3 | 5.2 | 8.9 | 5.4 | 5.8 |

TABLE No. 18-continued

Antibacterial (anti-*Chlamydia*) and immunomodulating (immuocorrecting) efficacy of the claimed medicinal preparation (in females with chronic inflammatory diseases of uterine appendages of the *Chlamydia* aetiology).

| Index: | | Basic antibacterial therapy, BAT (N = 15) | | BAT and the claimed medicinal preparation (N = 15) | | BAT and the prototype (N = 15) | |
|---|---|---|---|---|---|---|---|
| Gamma-interferon, produced by the peripheral blood leukocytes, and induced in culture by *staphylococcus* enterotoxin A, log$_2$ IU/ml, mean | 6.7 | 4.7 | 4.7 | 4.7 | 6.5 | 4.8 | 5.0 |

The data presented in Table No. 18 show that the claimed preparation is more effective, than the prototype, with lower rate of adverse effects. At that, the immune defense indices were significantly improved after carried out therapy with the claimed medicinal preparation, and this improvement is much more pronounced then those after the prototype treatment.

EXAMPLE 32

Antiviral Efficacy of the Medicinal Preparation (with Respect to Acute Viral Hepatitis A)

The claimed medicinal preparation was used in treatment of acute viral hepatitis A. 20 patients were enrolled in the trial. The patients were assigned randomly into two groups: 9 patients in the first group were receiving a medicinal preparation according to the invention and 11 patients in the second group were receiving the prototype. The preparations were administered intravenously in the dose of 250 mg (calculated based on 9-oxoacridine-10-acetic acid) once daily on the $1^{st}$, $2^{nd}$, $4^{th}$, $6^{th}$, $8^{th}$, $11^{th}$, $14^{th}$, $17^{th}$, $20^{th}$, $23^{rd}$ day (10 injections total) of the treatment course in monotherapy regimen. The efficacy of the therapy was estimated on the basis of the jaundice period duration, splenomegaly period duration, hepatomegaly, enzymemia (alanine aminotransferase) duration, dyspepsia. Before the initiation of the treatment, no statistically significant differences were noticed in patient distribution between the two groups in terms of sex, age, baseline enzyme level. The results of the study are presented in Table No. 19.

The data presented in Table No. 19 have shown that in the first group of patients that were treated with the claimed compound, the positive dynamics regarding biochemical and clinical indices, was expressed more significantly than in the second group of patients, treated with the prototype compound. Thus, the claimed compound is more effective in treatment of acute viral hepatitis A, than prototype, with lower rate of adverse events.

EXAMPLE 33

Antiviral Efficacy of the Claimed Medicinal Preparation (in the Treatment of Acute Viral Hepatitis B)

The claimed medicinal preparation was used in treatment of acute viral hepatitis B. Diagnosis of viral hepatitis was verified with the polymerase chain reaction (PCR) (detection of HBV DNA). A total of 45 persons were included in the trial. Patients were randomly assigned d into two groups: 24 persons in the group receiving the claimed medicinal preparation and 21 persons in the group, receiving the prototype. The preparations were administered intramuscularly in the dose of 250 mg or 500 mg (calculated as 9-oxoacridine-10-acetic acid) once daily on the $1^{st}$, $2^{nd}$, $4^{th}$, $6^{th}$, $8^{th}$, $11^{th}$, $14^{th}$, $17^{th}$, $20^{th}$, $23^{rd}$, $26^{th}$, $29^{th}$ day of the treatment course. Besides the therapy with preparations to be investigated, all the patients received the same basic therapy: disintoxication (Haemodez) and vitaminotherapy. The treatment efficacy was estimated on the basis of intoxication duration, liver dimensions normalization terms and biochemical and serological indices: hyperbilirubinemia and hyperenzymemia duration, TABLE No. 19

Antiviral efficacy of the medicinal preparation according to the invention in comparison to prototype (in respect of acute viral hepatitis A).

| Index | The claimed medicinal preparation (N = 9) | The prototype (N = 11) |
|---|---|---|
| Duration of the enzymemia period, days, mean | 20.3 | 25.3 |
| Duration of the hepatomegaly period, days, mean | 14.8 | 17.5 |
| Duration of the splenomegaly period, days, mean | 12.1 | 15.5 |
| Duration of the jaundice period, days, mean | 15.3 | 18.1 |
| Duration of the dyspepsia period, days, mean | 4.2 | 6.2 |
| Number of patients with adverse effects (temperature rise after the preparation injection), absolute value (percent) | 0 (0%) | 2 (22%) | terms of disappearance of HBsAg from the blood serum and appearance of the antibodies against HBeAg. Canges of serological markers (antigens: HBsAg, HBeAg; and antibodies: anti-HBcor IgM, anti-Hbco-total, anti-HBsAg, anti-HBeAg) were estimated with the immunoenzyme method. Before the treatment initiation, there were no statistically significant differences between the two groups in terms of enzyme, markers and viral load levels, in terms of received daily dose of preparation (250 mg or 500 mg), as well in terms of sex and age. The results of the study are presented in the Table No. 20.

TABLE No. 20

Antiviral efficacy of the claimed medicinal preparation (in treatment of acute viral hepatitis B).

| Index | Group of patients, receiving | |
|---|---|---|
| | The claimed medicinal preparation (N = 21) | The prototype (N = 24) |
| Duration of HBsAg persistence, days, mean | 22.1 | 29.1 |
| Appearance of anti-HBeAg and/or of anti-HBcor IgM, days, mean | 15.3 | 28.6 |
| Duration of the cytolysis period (hyperenzymemia), days, mean | 14.5 | 19.8 |
| Duration of the jaundice period, days, mean | 8.4 | 10.5 |
| Rate of the patients with HBV DNA in blood serum at the end of treatment, % | 0 | 16.7 |
| Rate of the patients with HBsAg in blood serum in 2.5 months after the end of treatment (chronization of the process), % | 0 | 12.5 |

In the group receiving the treatment with the claimed preparation, more pronounced positive dynamics concerning hepatitis B virus markers, and the jaundice period and cytolysis period were much shorter, than in the patient group receiving the prototype treatment. Besides, at examination of the patients in 2.5 months, in the group receiving the claimed medicinal preparation, no patients were found to be HBsAg carriers, and in the group receiving the prototype such patients were found, that declares that the claimed medicinal preparation, unlike the prototype, prevents the viral infection from becoming chronic. Thus, the claimed medicinal preparation is more effective in acute viral hepatitis B treatment, than the prototype, by lower rate of adverse events; and unlike the prototype, prevents viral infection from becoming chronic.

EXAMPLE 34

Antiviral Efficacy of the Claimed Medicinal Preparation (in Treatment of Acute Viral Hepatitis C)

The claimed medicinal preparation was used in treatment of acute viral hepatitis C. Diagnosis of viral hepatitis C was verified with the polymerase chain reaction. The therapeutic efficacy was estimated on the basis of the change of the rate of patients with different viral RNA blood levels (high, medium and low level, complete absence) and of the rate of patients with different serum alanine aminotransferase (ALT) levels: more than 7 upper normal limits (UNL) and higher, from 3 to 7 UNL, from 2 to 3 UNL, more than 1 but less than 2 UNL, from 1 and less UNL. Altogether, 42 patients were included in the trial. Patients were randomized into two groups: the group receiving the claimed medicinal preparation and the group receiving the prototype, correspondingly. The preparations were administered intramuscularly in the dose of 250 mg or 500 mg (calculated as 9-oxoacridine-10-acetic acid) once daily on the $1^{st}, 2^{nd}, 4^{th}, 6^{th}, 8^{th}, 11^{th}, 14^{th}, 17^{th}, 20^{th}, 23^{rd}, 26^{th}$ day of the treatment course (11 injections). Besides the therapy with the preparations to be compared all the patients received basic treatment with hepatoprotectors in identical doses (Phospholiv). One day before the treatment initiation and the next day after the course completion, in patients, the ALT level and the viral copies number in blood were determined. There were no statistically significant differences between groups before the treatment start in patient distribution in terms of daily received preparation dose (250 mg or 500 mg), of sex, age, ALT level, viral load, disease duration and viral genotype ("1b-genotype" and "not 1b genotype"). The results of the study are presented in the Table No. 21.

TABLE No. 21

Antiviral efficacy of the claimed medicinal preparation (at the treatment of acute viral hepatitis C).

| | Group of patients, receiving | | | |
|---|---|---|---|---|
| | The claimed medicinal preparation (N = 20) | | The prototype (N = 22) | |
| Index | Before treatment | After treatment | Before treatment | After treatment |
| Number of patients with high viral load (patients/%) | 10/50.0 | 0/0.0 | 11/50.0 | 1/4.5 |
| Number of patients with medium viral load (patients/%) | 5/25.0 | 0/0.0 | 6/27.3 | 5/22.7 |
| Number of patients with low viral load (patients/%) | 5/25.0 | 6/30.0 | 5/22.7 | 6/27.3 |
| Number of patients with no viral load (patients/%) | 0/0.0 | 14/70.0 | 0/0 | 8/36.4 |
| Number of patients with ALT level more than 7 UNL (patients/%) | 10/50.0 | 0/0.0 | 12/ | 0/0.0 |
| Number of patients with ALT level 3-7 UNL (patients/%) | 8/40.0 | 0/0.0 | 8/36.4 | 5/22.7 |
| Number of patients with ALT level 2-3 UNL (patients/%) | 2/10.0 | 2/10.0 | 2/9.1 | 10/45.5 |

TABLE No. 21-continued

Antiviral efficacy of the claimed medicinal preparation
(at the treatment of acute viral hepatitis C).

| | Group of patients, receiving | | | |
|---|---|---|---|---|
| | The claimed medicinal preparation (N = 20) | | The prototype (N = 22) | |
| Index | Before treatment | After treatment | Before treatment | After treatment |
| Number of patients with ALT level more than 1 but less than 2 UNL (patients/%) | 0/0.0 | 4/20.0 | 0/0.0 | 5/22.7 |
| Number of patients with ALT level 1 UNL and less (patients/%) | 0/0.0 | 14/70.0 | 0/0.0 | 2/9.1 |
| Number of patients in whom adverse events were noted (fewer after injection and/or allergic manifestations) (patients/%) | 0/0.0 | | 4/18.2 | |

* UNL—Upper Normal Limit of the corresponding index.

The data presented in the Table No. 21 show that the claimed medicinal preparation is more effective in acute viral hepatitis C treatment, than the prototype, with less rate of adverse events.

EXAMPLE 35

Antiviral Efficacy of the Claimed Medicinal Preparation (in Treatment of HIV-Infection)

The claimed medicinal preparation was used in treatment of HIV-infection (2A-3B stages). HIV-infection diagnosis was verified by checking of the presence of antibodies against HIV, and by the polymerase chain reaction. The claimed medicinal preparation or the prototype, were administered in enteric-coated tablets of 0.15 g (calculated as 9-oxoacridine-10-acetic acid). Patients took 4 tablets at once (that is 0.6 g per dose calculated as 9-oxoacridine-10-acetic acid) per os once a day on the $1^{st}$, $2^{nd}$, $4^{th}$, $6^{th}$, $8^{th}$, $11^{th}$, $14^{th}$, $17^{th}$, $20^{th}$, $23^{rd}$ day of treatment and then the same 4 tablets once every 3-5 days during 2.5 moths. Patients were randomized into two groups: the group, receiving the claimed medicinal preparation, and the group, receiving the prototype. In total 60 patients (30 in the group, receiving the claimed medicinal preparation and 30 in the group, receiving the prototype) were treated. A week before the treatment beginning, and a week after completing of the course, the number of virus copies in blood of patients was estimated. The therapy efficacy in corresponding group was estimated on the basis of the change of a rate of patients having different numbers of virus copies per milliliter of blood serum (under $1\times10^4$; from $1\times10^4$ to $3\times10^4$; from $3\times10^4$ to $1\times10^5$; above $1\times10^5$). Before the initiation of the treatment, there were no statistically significant differences of distribution between the two patients groups in terms of sex, age, viral load, disease duration and HIV stage. The results of the study are presented in the Table No. 22.

TABLE No. 22

Antiviral efficacy of the claimed medicinal
preparation (in treatment of HIV-infection).

| | Group of patients, receiving | | | |
|---|---|---|---|---|
| | The claimed medicinal preparation (N = 30) | | The prototype (N = 30) | |
| Index | Before treatment | After treatment | Before treatment | After treatment |
| Number of patients with viral load below $1 \times 10^4$ copies/ml (persons/%) | 10/33.3 | 22/73.3 | 11/36.6 | 14/46.7 |
| Number of patients with viral load from $1 \times 10^4$ to $3 \times 10^4$ copies/ml (persons/%) | 12/40.0 | 4/13.3 | 11/36.6 | 9/30.0 |
| Number of patients with viral load from $3 \times 10^4$ to $1 \times 10^5$ copies/ml (persons/%) | 5/16.7 | 3/10.0 | 6/20.0 | 5/16.7 |
| Number of patients with viral load above $1 \times 10^5$ copies/ml (persons/%) | 3/10.0 | 1/3.3 | 2/6.7 | 2/6.7 |
| Number of patients with observed adverse effects (body temperature rise after injection and/or allergic manifestations) (persons/%) | 0/0 | | 3/3.3 | |

TABLE No. 22-continued

Antiviral efficacy of the claimed medicinal preparation (in treatment of HIV-infection).

|  | Group of patients, receiving | | | |
|---|---|---|---|---|
|  | The claimed medicinal preparation (N = 30) | | The prototype (N = 30) | |
| Index | Before treatment | After treatment | Before treatment | After treatment |
| Number of patients with observed appearance of new HIV-associated infections during the treatment (persons/%) | 0/0 | | 4/13.3 | |

The data presented in the Table No. 22 show, that the claimed medicinal preparation is more effective in treatment of HIV and prophylactics of HIV-associated infections, than the prototype, with lower rate of adverse events.

EXAMPLE 36

Antiviral Efficacy of the Claimed Medicinal Preparation (in Treatment of Recurrent Genital Herpes)

51 patients (22 males and 29 females of 24 to 45 years old) with recurrent genital herpes, with mean duration of remission ranges from 1.5 to 2 months, recurrence rate 6 and more times annually, were included in the trial. Before the treatment, the relapse duration was 8-10 days. All the patients have passed the checkup, including physical examination, identification of the herpes simplex virus type 1 and 2 in samples of urogenital and foci discharges, using polymerase chain reaction (PCR) method. Before the admission for the treatment, patients were examined to ensure they no have other sexually transmitted diseases: syphilis, gonorrhea, trichomoniasis, Chlamydiosis, mycoplasmosis, urogenital candidosis. All the patients were randomized in two groups: the $1^{st}$ group received the claimed medicinal preparation, the $2^{nd}$ group received the prototype. Both preparations were injected intramuscularly in the dose of 250 g (calculated as 9-oxoacridine-10-acetic acid) once daily on the $1^{st}$, $2^{nd}$, $4^{th}$, $6^{th}$, $11^{th}$, $14^{th}$, $17^{th}$, $20^{th}$, $23^{rd}$ of the course of treatment (totally 10 injections for the course). Treatment was performed as monotherapy, beginning on a first day of the next relapse period. After the treatment course, patients were followed up via outpatient clinic visits during 6 months. The treatment efficacy criteria in each group were changes of rate of patients having various duration and frequency of relapses. Before the beginning of the treatment, there were no statistically significant differences in patient distribution between the two groups in terms of sex, age, frequency and duration of relapses. The results of the study of the antiviral efficacy of the claimed medicinal preparation are presented in the Table No. 23.

TABLE No. 23

Antiviral efficacy of the claimed medicinal preparation (in treatment of recurrent genital herpes).

|  | Group of patients, receiving | | | |
|---|---|---|---|---|
|  | The claimed medicinal preparation (N = 25) | | The prototype (N = 26) | |
| Index | Before treatment | After treatment | Before treatment | After treatment |
| Number of patients with relapse, during 4 days | 0/0.0 | 11/44.0 | 0/0 | 5/19.2 |
| Number of patients with relapse, during 5 days | 0/0.0 | 14/56.0 | 0/0 | 8/30.8 |
| Number of patients with relapse, during 6 days | 4/16.0 | 0/0.0 | 5/19.2 | 7/26.9 |
| Number of patients with relapse, during 7 days | 5/20.0 | 0/0.0 | 5/19.2 | 4/15.4 |
| Number of patients with relapse, during 8 days | 7/28.0 | 0/0.0 | 7/26.9 | 4/15.4 |
| Number of patients with relapse, during 9 days | 9/36.0 | 0/0.0 | 10/38.5 | 7/26.9 |
| Number of patients with relapse-free period of 6-7 weeks | 5/20.0 | 1/4.0 | 6/23.1 | 7/26.9 |
| Number of patients with relapse-free period of 7-8 weeks | 18/72.0 | 8/32.0 | 19/75.1 | 18/69.2 |

TABLE No. 23-continued

Antiviral efficacy of the claimed medicinal preparation
(in treatment of recurrent genital herpes).

|  | Group of patients, receiving | | | |
|---|---|---|---|---|
|  | The claimed medicinal preparation (N = 25) | | The prototype (N = 26) | |
| Index | Before treatment | After treatment | Before treatment | After treatment |
| Number of patients with relapse-free period of 9-10 weeks | 2/8.0 | 16/64.0 | 1/3.8 | 11/3.8 |
| Number of patients with observed adverse effects (body temperature rise after injection and/or allergic manifestations), absolute number (percent) | 1/4.0 | | 5/15.4 | |

* The absolute patient number is in the numerator, the general number percentage is in the denominator.

The data presented in the Table No. 23 show, that after the treatment with the claimed medicinal preparation the relapse duration significantly decreased, and the relapse-free period increased. At that, the prototype has had a lower influence on the relapse duration, and no influence on the relapse frequency. Besides, the significant decrease of inflammatory manifestation was estimated in treatment with the claimed medicinal preparation, and the rate of adverse events was lower than in group of patients treated with the prototype. Thus, the claimed medicinal preparation possesses a greater antiviral efficacy in treatment of recurrent genital herpes.

EXAMPLE 37

Antiviral Efficacy of the Claimed Medicinal Preparation (in Local Treatment of Orofacial Herpes)

74 patients (35 males and 39 females) of 18 to 55 years old with orofacial herpes were included in the trial. The diagnosis of herpetic infection was determined on the basis of the typical clinical presentation, and the diagnosis was verified by the observation of rising of antibodies titer against the herpes simplex virus in the paired sera using the immunoenzyme method. All the patients were randomized in two groups: the $1^{st}$ group received the claimed medicinal preparation, the $2^{nd}$ group received the prototype. Both preparations were applied locally as 5 mass % (calculated as 9-oxoacridine-10-acetic acid) liniment. Preparations were applied every time right after the herpes relapse manifestations (itch), and continue to apply (5 times daily) till the end of skin manifestations (scab) of each relapse. Treatment duration (supervision) was 6 months. Efficacy criteria were the duration of relapse of orofacial herpes, dynamics of foci number, dynamics of soreness periods, itch, burning, edema, and hyperemia durations. Before the beginning of the treatment, there were no statistically significant differences in patient distribution between the two groups in terms of sex, age, frequency and duration of relapses of orofacial herpes. The results of the study of the antiviral efficacy of the claimed medicinal preparation are presented in the Table No. 24.

TABLE No. 24

Antiviral efficacy of the claimed medicinal preparation
(in local treatment of orofacial herpes).

| Indices* | The claimed medicinal preparation | The prototype |
|---|---|---|
| Relapse duration (mean, days) | 15.3/7.7 | 14.4/10.2 |
| Foci number, mean | 8.5/7.0 | 8.3/8.1 |
| Soreness period duration, days, mean | 2.2/1.1 | 1.9/1.4 |
| Duration of itch and burning sensation, days, mean | 2.4/1.1 | 2.3/1.8 |
| Duration of edema, days, mean | 1.6/1.1 | 1.7/1.3 |
| Duration of hyperemia, days, mean | 1.7/1.0 | 1.7/1.5 |

*The parameter before the treatment is in nominator, the parameter after treatment is in denominator.

The data presented in the Table No. 23 show, that after treatment with the claimed medicinal preparation the relapse duration is significantly shorter, and the soreness, itch, burning sensation, edema and hyperemia periods are significantly shorter as well, than in treatment with the prototype. Besides, at the analysis of relapse frequency (a number of relapses in a year), there is a tendency to decrease the relapse frequency (from 7.2 to 6.8 in a year) in the group treated with the claimed medicinal preparation. There was no such effect in group, treated with the prototype. Thus, the claimed preparation is more effective in treatment of orofacial herpes, than the prototype.

EXAMPLE 38

Antiviral Activity of the Claimed Medicinal Preparation (in Treatment of Infectious Mononucleosis)

44 patients (30 males and 14 females) of 18 to 24 years old with typical clinical presentation of the disease (fever, tonsillitis, adenopathy, splenomegaly and hepatomegaly, rash), verified with laboratory (absolute lymphocytosis with presence of atypical forms) and serological tests (positive infectious mononucleosis test) were included into the trial. Patients were randomized in two groups: 22 patients were receiving the claimed medicinal preparation and 22 patients were receiving the prototype in equal single (=daily) dose of 250 mg (calculated as 9-oxoacridine-10-acetic acid) on the $1^{st}$, $2^{nd}$, $4^{th}$, $6^{th}$, $8^{th}$, $11^{th}$, $14^{th}$ day. Therapy efficacy was estimated on the basis of duration of fever, tonsillitis, adenopathy, splenomegaly and hepatomegaly periods. There were no differences in distribution between groups in terms of sex, age, severity level of the disease symptoms. The results of the study o are presented in the Table No. 25.

TABLE No. 25

Antiviral and immunomodulating activity of the claimed medicinal preparation (in treatment of infectious mononucleosis).

| Index | Group of patients, receiving | |
|---|---|---|
| | The claimed medicinal preparation (N = 22) | The prototype (N = 22) |
| Fever period duration, mean, days | 5.1 | 1.9 |
| Tonsillitis period duration, mean, days | 4.0 | 7.0 |
| Adenopathy period duration, mean, days | 7.4 | 11.5 |
| Splenomegaly period duration, mean, days | 7.0 | 14.2 |
| Hepatomegaly period duration, mean, days | 5.7 | 12.2 |
| Number of patients with observed adverse effects, caused by the treatment, absolute number (percent) | 0 (0%) | 2 (9.1%) |

The data presented in the table show, that in group of patients, treated with the claimed medicinal preparation, the period of pathological symptoms presence is much shorter, than in group of patients, treated with the prototype. Thus, the claimed medicinal preparation has a significantly higher efficacy in treatment of infectious mononucleosis, than the prototype, with lower rate of adverse events.

EXAMPLE 39

Antimicrobial and Immunomodulating Efficacy of the Claimed Compound (in Treatment of Purulent Diseases)

16 patients (10 males and 6 females) of 34 to 55 years old suffered from a mandibulofacial region phlegm were included in the trial. The patients were assigned randomly into two groups. Both groups were receiving the standard antibacterial therapy during 5 days (3 g of cefotaxime intramuscularly daily, divided into 4 injections). 8 patients received the prototype (group 1) and 8 patients received the claimed medicinal preparation. Preparations were taken as enteric coated tablets per os in equal single (=daily) dose of 600 mg (4 tablets of 0.15 g each, calculated as 9-oxoacridine-10-acetic acid) on the $1^{st}$, $2^{nd}$, $4^{th}$, $6^{th}$, $8^{th}$, $11^{th}$, $14^{th}$ day of treatment course. There were no differences in distribution between groups in terms of sex, age, severity level of the disease symptoms. The results of the study are presented in the Table No. 26.

TABLE No. 26

Antimicrobial and immunomodulating (immunocorrecting) efficacy of the claimed preparation (in treatment of purulent diseases).

| Index | Group 1 (the prototype + cefotaxime) (N = 8) | Group 2 (the claimed medicinal preparation + cefotaxime), (N = 8) |
|---|---|---|
| Period of fever, days after the beginning of the treatment, mean | 6 | 4 |
| Period of wound cleansing, days after the beginning of the treatment, mean | 8 | 4 |
| Period of wound healing, days after the beginning of the treatment, mean | 14 | 8 |
| Number of patients with developed resistance of microorganisms to the used antibiotic, absolute number (percent) | 2 (25%) | 0 (0%) |
| Index of phagocytic activity of the polymorphonuclear leukocytes to the end of the treatment, mean | 36 | 46 |

The data presented in the table show, that the claimed medicinal preparations is much more effectively, than the prototype, with the less number of adverse effects, possess a more expressed antimicrobial and immunocorrecting (immunomodulating) action on immunodeficiency, caused by infection, and also prevents the appearance of resistant strains of microorganisms.

EXAMPLE 40

Antifungal Activity of the Claimed Medicinal Preparation (in Treatment of Onychomycosis)

The claimed medicinal preparation was used in treatment of onychomycosis of hands and foots. 42 patients of 24 to 72 years old with duration of the disease more than 1.5 years were included in the trial. There were 8 patients with the distal lesions of hand, 4 patients with the proximal ones, 21 patients with the distal onychomycosis of the foot, 9 patients with the white foot onychomycosis. Patients were randomized into 2 groups: 22 patients in the group, receiving the claimed medicinal preparation and 20 patients in group, receiving the prototype. Both preparations were administered intramuscularly in the dose of 250 mg (calculated as 9-oxoacridine-10-acetic acid) once a day on the $1^{st}$, $2^{nd}$, $4^{th}$, $6^{th}$, $8^{th}$, $11^{th}$, $14^{th}$, $17^{th}$, $20^{th}$, $23^{rd}$ day of the course as the monotherapy. Sometimes, the application of the liniment of the claimed medicinal preparation or of the prototype on the affected area (5 mass %, calculated as 9-oxoacridine-10-acetic acid) was prescribed additionally in corresponding groups when a case of marked onychomycosis was revealed. Preparations were applied on the affected area twice a day during 1-20 days of the treatment course. At 10 days after the last injection, the treatment course was repeated. The result was estimated immediately after completion of the second treatment course (on the basis of the direct microscopy of the scraping material). There were no significant differences in distribution between groups in terms of sex, age, disease duration and therapy regimen. The results of the study are presented in the Table No. 27.

TABLE No. 27

Antifungal activity of the claimed medicinal preparation (in treatment of onychomycosis).

| Patients with: | Group of the patients, receiving | |
|---|---|---|
| | The claimed medicinal preparation (N = 22) | The prototype (N = 20) |
| hand distal onychomycosis | 4/3 (75%) | 4/2 (50%) |
| hand proximal onychomycosis | 2/1 (50%) | 2/0 (0%) |
| feet distal onychomycosis | 11/7 (66%) | 10/4 (40%) |
| white superficial onychomycosis of the feet | 5/3 (60%) | 4/1 (25%) |
| all types of the affect localization | 22/14 (64%) | 20/7 (35%) |
| with appeared adverse effects (subfebrile temperature and/or irritation) | 22/1 (5%) | 20/3 (15%) |

\* The total number of patients in sub-group is in the nominator, the number of cured patients is in denominator, the recovery percentage is in parentheses.

The data presented in the table show that the claimed medicinal preparation is more effective in treatment of mycotic lesions, than the prototype, with lower rate of adverse events. Thus, the claimed medicinal preparation is more effective in treatment of mycotic lesions, than the prototype, with lower rate of adverse events.

EXAMPLE 41

Antirheumatic and Antiphlogistic Activity of the Claimed Preparation (in Treatment of Rheumatoid Arthritis)

Antirheumatic and antiphlogistic activity of the claimed preparations was studied in treatment of rheumatoid arthritis (RA). 46 patients with RA of age from 22 to 54 years were submitted to the treatment. They have a disease duration ranging from 12 to 45 month. In all the patients, the active phase of the disease was observed: 20 patients had stage I, 23 patients had stage II, 3 patients had the stage III. RA of roentgenological grade I was observed in 21 patients, RA of grade II was observed in 17 patients, and 8 patients had RA of roentgenological grade III. Rheumatoid factor was determined in half of the patients. In most patients (86, 4%) had mainly the inflammatory rheumatic disease form with local exudative and exudative-proliferative changes. After the washing period (3 days) all the patients were randomized into two groups. The first group (23 patient) received the claimed medicinal preparation in single (=daily) dose of 250 mg (calculated as 9-oxoacridine-10 acetic acid) as 4 treatment courses with 14-day interval between each course (5 intramuscularly injections once daily on the $1^{st}$, $2^{nd}$, $4^{th}$, $6^{th}$, $8^{th}$ day of the course). The second group (23 persons) received the prototype in the same dose (calculated as 9-oxoacridine-10 acetic acid) and the injection regimen. The therapy efficacy was assessed by the dynamics of morning stiffness duration, number of inflamed joints, and pain intensity according to the Visual Analogue Scale (VAS) of pain. The claimed medicinal preparation decreased the intensity of subjective and objective symptoms of joints inflammation: the pain intensity, the number of swollen joints, erythrocyte sedimentation rate and the level of the rheumatoid factor in blood decreased considerably. The prototype has had a lower influence on the indicated parameters. The results of the study are presented in Table No. 28.

TABLE No. 28

Antirheumatic and antiphlogistic activity of the claimed preparation (in treatment of rheumatoid arthritis).

| | Group | | | |
|---|---|---|---|---|
| | The claimed medicinal preparation (N = 23) | | The prototype (N = 23) | |
| Index | Before the treatment | After the treatment | Before the treatment | After the treatment |
| Number of inflamed joints, mean | 4.7 | 2.7 | 4.4 | 3.5 |
| Pain Intensity according to the Visual Analogue Scale (VAS), mean, cm | 9.6 | 6.1 | 9.3 | 7.7 |
| Duration of the morning stiffness, mean, hrs | 3.9 | 1.6 | 3.8 | 2.6 |
| Responders, absolute number (percent) | 10 (43.5%) | | 6 (26.1%) | |
| Number of patients with observed adverse effects (allergic reactions and/or the temperature rise after the preparation injection), absolute number (percent) | 0 (0%) | | 4 (17.4%) | |

Thus, the claimed medicinal preparation has a more expressed antirheumatic and antiphlogistic activity and it provokes fewer adverse events, than the prototype,

EXAMPLE 42

Antidystrophic and Antiphlogistic Efficacy of the Claimed Preparation (in Treatment of Knee Joint Osteoarthrosis)

The efficacy of the claimed medicinal preparation at the degenerative-dystrophic affection of knee-joint was demonstrated in the case of knee joint osteoarthrosis (OA). Patients 45-65 years age, with verified diagnosis of the one-sided primary (idiopathic) knee joint OA or posttraumatic OA having stage II of OA (Kellgren & Lawrence grade), were included in the trial. All the patients (42 persons) were randomized in two groups (21 persons in each). During 2 weeks before the beginning of the treatment, all the patients did not receive any preparations of OA specific treatment, including nonsteroid antiphlogistic preparations (washing period). Then all patients were examined with the pain visual analogue scale (VAS) and the knee-joint functional activity scale Knee injury and Osteoarthritis Outcome Score (KOOS). Patients of both groups had similar parameters of clinical presentations intensity and similar knee joint OA severity grade. The claimed medicinal preparation or the prototype, respectively, were administered intramuscularly in the single dose of 250 mg (calculated as 9-oxoacridine-10 acetic acid) in 2 courses of 5 injections on the $1^{st}$, $2^{nd}$, $4^{th}$, $6^{th}$, $8^{th}$ day with an interval of 14 days between courses. Both groups received as the basic chondroprotective therapy the chondroitin sulfate (Structum) preparation in daily dose of 1000 mg (1 tablet of 500 mg, twice a day). Therapy efficacy was estimated as "responders" rate. Treatment effect was considered "response" if the decrease of the KOOS on 20 or more score points and/or decrease of VAS value on 2 cm or more to the end of the treatment were observed. The results of the study are presented in Table No. 29.

TABLE No. 29

Antidystrophic and antiphlogistic efficacy of the claimed preparation (in treatment of knee-joint osteoarthrosis)

| Index | Group of the patients, receiving | |
|---|---|---|
| | The claimed medicinal preparation (N = 21) | The prototype (N = 21) |
| "Responders" according to the visual analogue scale (VAS), % | 90.4 | 38.1 |
| "Responders" according to the functional activity scale (KOOS), % | 81.0 | 23.9 |
| Responders according to the both scales, % | 76.2 | 19.0 |
| Rate of the patients with adverse effects (allergic reactions and fever after injection), % | 0 | 14.3 |

The data presented in the Table No. 29 show that the knee-joint inflammation symptoms, pain and motor disturbances are significantly less expressed in the group, treated with the claimed medicinal preparation, responders rate is higher, than in group, receiving the prototype. Thus, the claimed medicinal preparation is significantly more effective in treatment of degenerative-dystrophic pathology of joints, than the prototype; and the frequency of adverse events is less than those observed for the prototype.

EXAMPLE 43

Antiphlogistic, Immunocorrecting and Antibacterial Efficacy of the Claimed Medicinal Preparation (in Treatment of Nonspecific Chronic Prostatitis)

The claimed medicinal preparation was used in treatment of nonspecific chronic prostatitis. 60 males of 22 to 64 years old with nonspecific chronic prostatitis in torpid and latent inflammation phase were included in the trial. The diagnosis was verified by the bacteriological test, clinical and laboratory indices and the ultrasound study. The patients were assigned randomly into two groups: 32 patients in the group receiving the claimed medicinal preparation and 28 patients in the group receiving the prototype. Preparations were administered rectal as suppositories in the dose of 250 mg (calculated as 9-oxoacridine-10 acetic acid) once daily on the $1^{st}$, $2^{nd}$, $4^{th}$, $6^{th}$, $8^{th}$, $14^{th}$, $17^{th}$, $20^{th}$, $23^{rd}$ day of treatment course in monotherapy regimen. Therapy efficacy was estimated on the $15^{th}$ day after the beginning of treatment according to the dynamics of the National Institutes of Health Chronic Prostatitis Symptoms Index (NIH-CPSI), and also upon the change of the rate of patients with bacteriuria. The immunological indices were also estimated before and after the treatment: dynamics of the level of blood serum proinflammatory cytokines—tumor necrosis factor-alpha (TNF-alpha), interleukine—1-beta (IL-1-beta), interleukine-6 (IL-6) and antiphlogistic cytokine—interleukine 4 (IL-4). The level of cytokines was determined by the ELISA method. Also the phagocytic activity of peripheral blood neutrophils was estimated before and after the treatment, namely the phagocytosis percent and the phagocytic number. According to the index normalization rate, the therapy efficacy was estimated as "excellent" decrease of NIH-CPSI index more than in 3 times, "good"—decrease of NIH-CPSI index in 2-3 times, "satisfactory"—decrease of NIH-CPSI index in 1.5-2 times and "no effect"—decrease of NIH-CPSI index is below 1.5 times. There were no statistically significant differences between groups before the treatment start in patient distribution in terms of NIH-CPSI index, sex, age, presence of bacteria in urine. The results of the study are presented in the Table No. 30.

TABLE No. 30

Antiphlogistic, immunocorrecting and antibacterial efficacy of the claimed medicinal preparation (in treatment of nonspecific chronic prostatitis).

| Effect/index* | Group of patients, receiving | |
|---|---|---|
| | The claimed medicinal preparation (N = 32) | The prototype (N = 28) |
| Excellent, absolute number (percent) | 4 (12.3) | 0 (0%) |
| Good, absolute number (percent) | 26 (81.3%) | 2 (7.1%) |
| Satisfactory, absolute number (percent) | 2 (6.3%) | 15 (53.6%) |
| No effect, absolute number (percent) | 0 (0%) | 11 (39.2%) |
| Urine sanation, absolute number | у 23 из 28 | у 8 из 22 |
| TNF-alpha in serum, pg/ml (before treatment/after treatment) | 315.4/72.1 | 325.7/156.3 |
| IL-1-beta in serum, pg/ml (before treatment/after treatment) | 78.7/45.1 | 74.2/58.3 |
| IL-6 in serum, pg/ml (before treatment/after treatment) | 569.9/286.4 | 578.3/368.3 |
| IL-6 in serum, pg/ml (before treatment/after treatment) | 43.6/92.1 | 44.2/69.4 |
| TNF-alpha in prostate secret, pg/ml (before treatment/after treatment) | 36.3/15.5 | 37.5/21.3 |
| IL-1-beta in prostate secret, pg/ml (before treatment/after treatment) | 13.7/6.8 | 12.9/9.1 |
| IL-6 in prostate secret, pg/ml (before treatment/after treatment) | 507.4/342.6 | 499.2/401.3 |
| IL-4 in prostate secret, pg/ml (before treatment/after treatment) | 27.4/78.5 | 29.3/69.3 |
| Phagocytosis percent, % (before treatment/after treatment) | 42.1/64.4 | 38.9/46.3 |
| Phagocytic number, absolute (before treatment/after treatment) | 4.2/6.9 | 4.5/5.3 |
| Adverse events, absolute number (percent) | 7 (21%) | 0 (0%) |

*For the laboratory indices the mean values are stated.

In group, treated with the claimed medicinal preparation, the positive dynamics was more expressed, regarding clinical indexes, than in the group of patients, receiving the treatment with prototype. At that, the proinflammatory cytokines level both in blood and in prostate secret decreased, and the level of antiphlogistic, on the contrary, increased, and the said dynamics was more expressed in the group of patients, treated with the claimed preparation, than in group, treated with the prototype. In 82% of all patients in the group, treated with the claimed medicinal preparation, the disappearance of pathogen from the urine is registered, whereas in the group treated with the prototype it was registered only in 30% of all patients. Thus, the claimed medicinal preparation possesses a greater antiphlogistic, immunocorrecting and antibacterial efficacy, than the prototype, and is more effective in treatment of prostatitis, than the prototype, with a less rate of adverse events.

EXAMPLE 44

Antitumor Efficacy of the Claimed Medicinal Preparation (in Treatment of Non-Hodgkin's Lymphomas)

The claimed medicinal preparation was used in complex treatment of non-Hodgkin's lymphomas, comparing with the prototype. 54 persons of 36 to 80 years old with morphologically verified diagnosis and the intermediate malignancy rate were included in trial. The patients were assigned randomly into two groups: 27 patients in the group receiving the claimed medicinal preparation and 27 patients in the group receiving the prototype. The preparations were administered intramuscularly in the dose of 500 mg (calculated as 9-oxoacridine-10-acetic acid) once daily on the $1^{st}$, $2^{nd}$, $4^{th}$, $6^{th}$, $8^{th}$, $11^{th}$, $14^{th}$, $17^{th}$ day of the treatment course. Besides, both groups received the basic induction polychemotherapy (PChT) in the ACOP scheme (cyclophosphan—750 mg/m$^2$ intravenously in the $1^{st}$ day, vincristin—1.4 mg/m$^2$ intravenously in the $1^{st}$ day, adriamycin—50 mg/m$^2$ intravenously in the $1^{st}$ day, prednisolone—60 mg/m$^2$ daily, per os, from $1^{st}$ to the $5^{th}$ day of the course). Interval between PChT courses was 21 days. Treatment consisted of 6-8 chemotherapy courses. Then the patients received the irradiation of areas, included in the process, in summary basic dose of 30-50 Gy. The estimation of the response was carried out according the recommendations of International Working Group to Standardize Response Criteria for Non-Hogkin's Lymphomas, 1999>>. There were no differences between groups in patient distribution in terms of sex, age, common status upon the ECOG grade, patient rate with extra nodal affections and in stage of disease. The results of the study are presented in the Table No. 31.

TABLE No. 31

Antitumor efficacy of the claimed medicinal preparation (in treatment of non-Hodgkin's lymphomas).

| Index (number of patients in group with observed)*: | Group of patients, receiving | |
|---|---|---|
| | The claimed medicinal preparation + PChT (N = 27) | The prototype + PChT (N = 27) |
| Complete or Unproved complete response | 14 (51.9%) | 11 (40.7%) |
| Partial response | 7 (25.9%) | 5 (18.5%) |
| Stabilization | 2 (7.4%) | 5 (18.5%) |
| Progress (no response) | 4 (14.8%) | 6 (22.2%) |
| Allergic adverse events | 1 (3.7%) | 6 (22.2%) |

*The percent of the total number of patients in a group is in parentheses.

The data presented in Table 31 show, that in group, receiving the claimed medicinal preparation, the patient rate with complete response is higher, than in the group of patients, receiving the prototype, and the patients rate with no response is lower. The rate of adverse events (allergic manifestations) was lower in the group, receiving the claimed preparation, than in the group, receiving the prototype. Thus, the claimed medicinal preparation is more effective in treatment of tumors, than the prototype, with lower rate of adverse events.

EXAMPLE 45

Prophylactic Antiviral Efficacy of the Claimed Medicinal Preparation (in Prophylaxis of Acute Respiratory Viral Infections (ARVI) and Grippe)

Prophylactic efficacy of the claimed medicinal preparation in comparison with the prototype was estimated upon the frequency of diseased with grippe and ARVI patients in group, receiving, respectively, the claimed medicinal preparation and the prototype, and the group of patients, that are not receiving the drugs in the epidemiological season. The claimed medicinal preparation or the prototype, respectively, were administered per os as tablets in dose of 0.15 g (calculated as 9-oxoacridine-10-acetic acid) on the $1^{st}$, $2^{nd}$, $4^{th}$, $6^{th}$, $8^{th}$ day of the treatment course and then another 5 doses with an interval of 72 hours. To children of 4 to 6 years old one tablet was administered; children of 7 to 11 years old received one or two tablets, children older than 12 years received 3 or 4 tablets once daily; adults were administered with from 1 to 4 tablets (i.e., for example the single dose could be 0.5 mg/kg). The distribution in terms of sex, age, single and course dose in all groups was similar. The results of the study are presented in the Table No. 32.

TABLE No. 32

Prophylactic antiviral efficacy of the claimed medicinal preparation (in prophylaxis of acute respiratory viral infections (ARVI) and grippe)

| Group | Number of persons | Diseased with grippe or ARVI from XII-03 r. till II-04r. | Index on 100 persons | Number of registered adverse events |
|---|---|---|---|---|
| No preparation received (control) | 55 | 40 | 72.7 | — |
| Received the course of the claimed medicinal preparation | 60 | 11 | 18.3 | 0 |
| Received the course of the prototype | 54 | 35 | 64.8 | 4 |

The data presented in Table 32 show that in the epidemiological season the morbidity with grippe and ARVI among persons, that have not received the prophylactic preparations was high (72.7%). Morbidity in the group, that received the prototype was lower (64.3%). In the group, that received the claimed medicinal preparation the morbidity with the grippe and ARVI was only 18.3%. When the claimed medicinal preparation was administrated as a prophylactic remedy, there were no unusual general and local reactions; in 4 patients received the prototype the temperature rise (3 persons) and urticaria (1 person) was observed. Thus, the claimed medicinal preparation possesses a significantly greater prophylactic antiviral efficacy, than the prototype, with lower rate of adverse events.

EXAMPLE 46

Prophylactic Antifungal Efficacy of the Claimed Medicinal Preparation (in Prophylaxis of the Fungal Infections)

To study the prophylactic antifungal efficacy of the claimed medicinal preparation in comparison with the prototype, the trial in patients, being on the treatment in the intensive care departments (totally 60 persons) at least than 7 days, was performed. In the trial were included patients with a high risk of fungal infection development and having any of following conditions (or their combinations): intestinal perforation, anastomotic breakdown of digestive tract, secondary disseminated peritonitis, surgical operations on pancreas, pancreonecrosis, condition after splenectomy, prolonged (more than a week) artificial lung ventilation, prolonged (more than a week) parenteral nutrition, multiple organ failure (disfunction of more than two systems), immunocompromised conditions (for example, prolonged corticosteroid therapy). Patients were assigned randomly into two groups: one group receiving the prototype and the second group receiving the claimed medicinal preparation. Criteria of the development of the fungal infection were any of subsequent: candiduria, single detection of Candida blood, detection of Candida in the any sterile anatomic region (except urine), microscopy identification of fungi from any biological materials. The claimed preparation or the prototype was taken per os. Preparations were administered as enteric coated tablets, or parenteral (intramuscular) at dose of 3-10 mg/kg (calculated as 9-oxoacridine-10-acetic acid residue) once daily on the $1^{st}$, $2^{nd}$, $4^{th}$, $6^{th}$, $8^{th}$, $11^{th}$ day a of the treatment course. Patients have not received any specific antifungal agents. The frequency of fungal infection development was estimated. The results of the study are presented in the Table No. 32.

TABLE No. 32

Prophylactic antifungal efficacy of the claimed medicinal preparation (in prophylaxis of the fungal infections).

| Group, | Number of patients in the group | Number of patients with developed fungal infection |
|---|---|---|
| Received the course of the claimed medical preparation | 32 | 1 |
| Received the course of the prototype | 28 | 8 |

The data presented in the table 32 show that the frequency of fungal infection development in group of patients, that received the claimed medicinal preparation, was lower than in group that received the prototype.

EXAMPLE 47

Prophylactic Antimicrobial Efficacy of the Claimed Medicinal Preparation (in Prophylaxis of Proinflammatory Processes)

Examination of the prophylactic antimicrobial activity of the claimed medicinal preparation in comparison with the prototype was performed in patients with lower jaw fracture that sought medical advice in later terms (4-6 days) after the beginning of the disease. Patients have received the classical orthopedic treatment with reposition and splintage. Patients were assigned randomly into two groups. To the one group the claimed medicinal preparation was administered right after the admission to the hospital, to the another the prototype was administered in the same dose: 8 mg/kg body weight at once (calculated as 9-oxoacridine-10-acetic acid) intravenously. Patients have not received the specific antimicrobial preparations. After the surgery the frequency of purulent complications development (including gingivitis and osteomyelitis). The results of the study are presented in the Table No. 33.

TABLE No. 33

Prophylactic antimicrobial efficacy of the claimed medicinal preparation (in prophylaxis of proinflammatory processes).

| Group, | Number of patients in the group | Number of patients with developed microbial (purulent) infection |
|---|---|---|
| Received the course of the claimed medical preparation | 14 | 4 |
| Received the course of the prototype | 15 | 8 |

The data presented in the Table No. 33 show, that the frequency of development of the microbial infection in the group of patients, that received the claimed medicinal preparation was significantly lower, than in group, that received the prototype.

EXAMPLE 48

Medicinal and Prophylactic Antiparasitic Efficacy of the Claimed Medicinal Preparation (at the Enterobiasis)

In the trial were included 42 children (7-13 years old) with enterobiasis, detected microscopically using the M.C. Hall method by the perianal scrape with the cellophane bit, that was microscopically evaluated to detect and identify the eggs of Enterobius (Oxyuris) vermicularis. Material was collected and examined three times with a one day interval. Among the infested children, the clinical manifestations were detected in 10 cases as perianal itch (5 persons), hyperemia of perianal lines (1 person), anorexia (1 person). In 12 children the invasion was proceeding on the unfavorable background (refractory course of the enterobiasis, bad obstetric-gynecologic anamnesis, perinatal affections of the central nervous system, frequent acute respiratory diseases). Patients were assigned into two groups by the random sampling from 44 persons with monoinvasion. The first group (20 persons—11 boys and 9 girls) took the claimed medicinal preparation as enteric-coated tablets in dose of 0.15 g (calculated as 9-oxoacridine-10-acetic acid) at once in an hour after the breakfast; the tablets were swallowed without chewing. Daily dose (=single dose) was 0.3 g (=2 tablets) for children from 7 to 10 years old or 0.6 g (=4 tablets) for children older than 10 years (i.e., for example, at the bodyweight 10 kg, the single dose was up to 30 mg/kg). The second group (22 persons—10 boys and 12 girls) took the prototype as enteric-coated tablets in dose of 0.15 g (calculated as 9-oxoacridine-10-acetic acid) at once in an hour after the breakfast; the tablets were swallowed without chewing. Daily dose (=single dose) was 0.3 g (=2 tablets) for children from 7 to 10 years old or 0.6 g (=4 tablets) for children older than 10 years. There were no differences in children distribution in age, sex, compromised anamnesis. The carried out therapy efficacy was established upon nine control examinations of faeces on the presence of helminth eggs using the method of A. Davis (Davis A., Drug Treatment in Intestinal Helminthiasis, WHO, 1973.) on the $8^{th}$-$14^{th}$ day (early therapeutic effectiveness), $16^{th}$-$21^{th}$ day (later therapeutic effectiveness) and on the $50^{th}$-$57^{th}$ (remote therapeutic effectiveness) after the treatment course with intervals of 1-2 days. Epidemiological (prophylactic) effect of treatment was estimated upon the reinvasion frequency (repeated contagion), that was determined as a percent of newly infested from the number of recovered children. The results of the study are presented in the Table No. 34.

prototype, respectively) was started 7 days prior to a next PChT course start date; the preparations were administered once daily by intravenous bolus injection every two days at daily dose 10 mg/kg body weight until the completion of PChT course.

The comparative appraisal comparative appraisal of the prophylactic efficacy of the claimed medicinal preparation regarding to hematological and other types of toxic effects, caused by the PChT, was performed on the basis of the analysis of the patient rate in each group with registered toxic effects of PChT. The toxicity rate was established according to the toxicity criterions of WHO. The groups of patients were similar in terms of sex, age, disease stage, process morbidity, Karnofsky and ECOG indexes. The results of the study are presented in the Table No. 35.

TABLE No. 34

Medicinal and prophylactic antiparasitic efficacy of the claimed medicinal preparation (at the enterobiasis).

| Group of children, that received Analysis realization terms | Absence of *Enterobius* (Oxyuris) *vermicularis* eggs* | | | Percentage of newly infested |
|---|---|---|---|---|
| | on the $8^{th}$-$14^{th}$ day (early therapeutic effectiveness) | on the $16^{th}$-$21^{th}$ day (later therapeutic effectiveness) | on the $50^{th}$-$57^{th}$ (remote therapeutic effectiveness) | |
| The claimed medicinal preparation (N = 20) | 20/100% | 20/100% | 17/85% | 11/65% |
| The prototype (N =22) | 14/64% | 17/77% | 10/45% | 4/40% |

*The absolute number of patients is in nominator, the percent from the total number in a group is in the denominator.

The data presented in the table 34 show that the claimed medicinal preparation possesses a greater antiparasitic efficacy, than the prototype, both in treatment of parasitic invasion and in prophylaxis of reinvasion of parasites.

EXAMPLE 49

Clinical Efficacy of the Claimed Medicinal Preparation in Prophylaxis of Hematologic and Other Types of Toxicity Caused by Chemotherapy 62 patients (34 males and 28 females) with verified diagnosis of non-small cell lung cancer of the IIIb-IVb stages (T2N1M0-T3N2M1) were added in the trial. All patients were randomly assigned in 3 groups: $1^{st}$ groups (21 persons) received the claimed medicinal preparation as before as well during the course of the polychemotherapy (PChT); the $2^{nd}$ group (21 persons) received the prototype as before as well during the course of the PChT; the $3^{rd}$ group (20 persons) received only PChT. The PChT course was performed according this regimen: cisplatin intravenously on the $4^{th}$ day of the course at dose of 80 mg/m$^2$, etoposide intravenously at dose of 100 mg/m$^2$ from the $1^{st}$ to the $3^{rd}$ day, nitrulline on the $5^{th}$ day of the course at dose of 300 mg/m$^2$. All the patients received 3 courses of PChT. The administration of both preparations (of the claimed medicinal preparation and of the TABLE No. 35

Clinical efficacy of the claimed medicinal preparation in prophylaxis of hematologic and other types of toxicity caused by chemotherapy.

| | Number of patients with I-IV stage of toxicity upon the toxicity WHO scale* | | |
|---|---|---|---|
| Toxicity type | Group 1, PChT + the claimed medicinal preparation (N = 21) | Group 2, PChT + the prototype (N = 21) | Group 3, PChT (N = 20) |
| Anemia | 6 (28.6%) | 8 (38.1%) | 10 (50.0%) |
| Leukopenia | 7 (33.3%) | 10 (47.6%) | 13 (65.0%) |
| Neutropenia | 5 (23.8%) | 10 (47.6%) | 12 (60.0%) |
| Thrombocytopenia | 3 (14.3%) | 4 (19.0%) | 5 (25.0%) |
| Nausea/Vomiting | 3 (14.3%) | 8 (38.1%) | 14 (70.0%) |
| Diarrhea | — | 1 (4.8%) | — |
| Nephrotoxicity | 1 (4.8%) | 3 (14.3%) | 5 (25.0%) |
| Neurotoxicity | 1 (4.8%) | 2 (9.5%) | 3 (15.0%) |

*Absolute number in a group (percent is in parantheses)

The data presented in the Table No. 35 show that the main type of the toxicity of the carried out PChT was the hematological toxicity. Neutropenia was marked in 23.8% of patients of the $1^{st}$ group, in 47.6% of patients of the $2^{nd}$ group and in 60.0% of the $3^{rd}$ group. Nephrotoxicity was marked in 4.8% of the $1^{st}$ group, in 14.3% of patients of the $2^{nd}$ group and in 25.0% of the $3^{rd}$ group. The same regularity was marked in prophylaxis of the PChT neurotoxicity. The claimed medicinal preparation effectively prevented from the manifestations (to a greater extent) of the hematological toxicity, and also (in lesser extent) from other types of toxicity. The prototype possessed a significantly lower ability regarding the prophylaxis of these toxic effects. Thus, the claimed medicinal preparation possesses significantly greater clinical efficacy, than the prototype, in prophylaxis of the hematological and other types of toxicity, caused by the chemotherapy of malignant tumors.

EXAMPLE 50

The clinical efficacy of the claimed medicinal preparation in prophylaxis and treatment of radiotherapy complications. 46 female patients suffering from uterine body cancer at stages Ib-II were included in the efficacy study of the claimed medicinal preparation in prophylaxis and treatment of radiotherapy complications. All the patients were randomized into two equal groups.

One week before surgery, one group (the treatment group) began to receive the claimed medicinal preparation intramuscularly in dose of 250 mg (calculating as 9-oxoacridin-10-acetic acid) on the 1st, 2nd, 4th, 6th day (one week before surgery), and then on the 1st, 2nd, 4th, 6th day after surgery. The other group (control group) received the prototype in the same dose (calculating as 9-oxoacridin-10-acetic acid), with the same regimen and by the same administration route. In all the patients, an extensive extirpation of the uterus with adnexa was performed with 6 MeV fast electron beam intraoperative irradiation to single dose of 12 Gy to a vaginal remnant. The procedure was carried out with protective shielding of urinary bladder and rectum. During the post-op period, all the patients received gamma-therapy at standard regimen of dose fractionation: single focal dose was 2.0 Gy, 5 fractions a week; summary focal dose was 44-46 Gy to the parametrium area. The course summary dose was 62 Gy as iso-effect, taking into account the intraoperative irradiation of 12 Gy and duration of treatment interruption after surgery. The prophylactic efficacy of the claimed medicinal preparation was assessed by the frequency of early radioreactions events as cystitis and rectitis, and the medical efficacy was estimated by the terms of these complications relief. The distribution of patients of both groups in terms of the disease stage, the age and disease duration was similar. In the treatment group the frequency of radiation rectitis and proctitis was 13.0 and 17.4%, correspondingly, and in the control group it was 43.5% and 52.2%. Mean terms of the radiation rectitis and cystitis symptoms relief (in common) in the patient group, receiving the claimed medicinal preparation were 1.5 times shorter, than in patients of the control group. Thus, the claimed medicinal preparation shows a high efficacy both in prophylaxis and in treatment of complications, arising due to the radiotherapy, and these properties of the claimed medicinal preparation are more pronounced than those of the prototype.

The invention claimed is:
1. Salts of 1-alkylamino-1-deoxypolyols and 9-oxoacridine-10-acetic acid of the general formula (I):

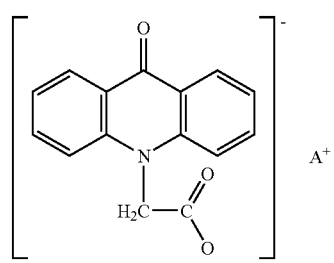

(I)

wherein A+ is (II)

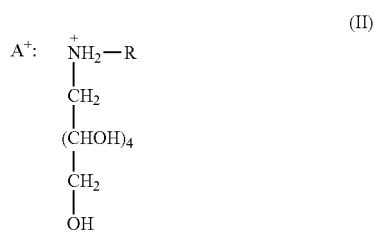

(II)

wherein R is selected from the group consisting of: ethyl; propyl; and butyl.

2. Salts of claim 1 possessing activity selected from the group consisting of: immunomodulating, immunocorrecting, antiparasitic, antisclerotic, antiviral, antibacterial including anti-Chlamydia, antifungal, antiphlogistic, antitumor, radioprotective and stressprotective activities.

3. A salt of claim 1, which is selected from the group consisting of:

N-(1-deoxy-D-glucitol-1-yl)-N-ethyl ammonium 9-oxoacridine-10-ylacetate;

N-(1-deoxy-D-glucitol-1-yl)-N-propyl ammonium 9-oxoacridine-10-ylacetate;

N-(1-deoxy-D-glucitol-1-yl)-N-butyl ammonium 9-oxoacridine-10-ylacetate;

N-(1-deoxy-D-galactitol-1-yl)-N-ethyl ammonium 9-oxoacridine-10-ylacetate;

N-(1-deoxy-D-galactitol 1-1-yl)-N-propyl ammonium 9-oxoacridine-10-ylacetate;

N-(1-deoxy-D-galactitol-1-yl)-N-butyl ammonium 9-oxoacridine-10-ylacetate;

N-(1-deoxy-D-mannitol-1-yl)-N-ethyl ammonium 9-oxoacridine-10-ylacetate;

N-(1-deoxy-D-mannitol-1-yl)-N-butyl ammonium 9-oxoacridine-10-ylacetate;

N-(1-deoxy-L-glucitol-1-yl)-N-ethyl ammonium 9-oxoacridine-10-ylacetate;

N-(1-deoxy-L-glucitol-1-yl)-N-propyl ammonium 9-oxoacridine-10-ylacetate;

N-(1-deoxy-L-glucitol-1-yl)-N-butyl ammonium 9-oxoacridine-10-ylacetate;

N-(1-deoxy-L-galactitol-1-yl)-N-ethyl ammonium 9-oxoacridine-10-ylacetate;

N-(1-deoxy-L-galactitol-1-yl)-N-propyl ammonium 9-oxoacridine-10-ylacetate;

N-(1-deoxy-L-galactitol-1-yl)-N-butyl ammonium 9-oxoacridine-10-ylacetate;

N-(1-deoxy-L-mannitol-1-yl)-N-ethyl ammonium 9-oxoacridine-10-ylacetate;

N-(1-deoxy-L-mannitol-1-yl)-N-propyl ammonium 9-oxoacridine-10-ylacetate; and

N-(1-deoxy-L-mannitol-1-yl)-N-butyl ammonium 9-oxoacridine-10-ylacetate.

4. A medicinal preparation comprising an active ingredient in an effective dose and a pharmaceutically acceptable vehicle or a diluent, wherein said active ingredient comprises one or more of salts of formula (I) according to claim 1 and/or a mixture of said salt of formula (I) or 9-oxoacridine-10-acetic acid of the general formula (III):

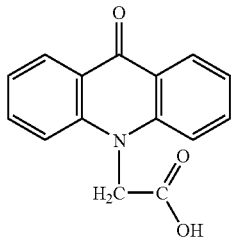

(III)

and one or more 1-alkylamino-1-deoxypolyols or the general formula (II):

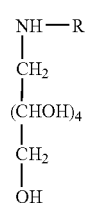

(II)

wherein R is selected from the group consisting of ethyl, propyl, and butyl.

5. A medicinal preparation of claim 4, wherein said medicinal preparation possesses activity selected from the group consisting of immunomodulating, immunoconecting, antiparasitic, antisclerotic, antiviral, antibacterial, including antichlamydia, antifungal, antiphlogistic, antitumor, radioprotective, and stressprotective effects.

6. A medicinal preparation of claim 4, wherein said medicinal preparation is obtained by mixing 9-oxoacridine-10-acetic acid of the formula (III) and one or more 1-alkylamino-1-deoxypolyols of the general formula (II) at the ratio of 9-oxoacridine-10-acetic acid to 1-alkylamino-1-deoxypolyol in the mixture of 1.2:1 to 1:1.1.

7. A medicinal preparation of claim 4, wherein said medicinal preparation is obtained by mixing a salt of formula (I) and one or more 1-alkylamino-1-deoxypolyols of the general formula (II) at the ratio of the salt of formula (I) to 1-alkylamino-1-deoxypolyol in the mixture of 220:1 to 1:1:1.1.

8. A medicinal preparation of any one of claims 4-7 in dosage form adapted for parenteral use.

9. A medicinal preparation of claim 8, wherein said medicinal preparation comprises salts of formula (I) or the mixtures of 9-oxoacridine-10-acetic acid of formula (III) or a salt of formula (I) and one or more 1-alkylamino-1-deoxypolyol of the general formula (II), in amount of 9.0-28.0 mass %; the balance being water for injection.

10. A medicinal preparation of claim 8, wherein said medicinal preparation comprises a mixture of 9-oxoacridine-10-acetic acid and 1-deoxy-1-N-(ethylamino)-D-glucitol with the components weight ratio from 1.2:1 to 1 to 1:1.1, in amount of 9.0-28.0 mass %; the balance being water for injection.

11. A medicinal preparation of claim 8, wherein said medicinal preparation comprises a mixture of N-(1-deoxy-D-glucitol-1-yl)-N-ethyl ammonium 9-oxoacridine-10-ylacetate and 1-deoxy-1-N-(ethylamino)-D-glucitol at the weight ratio of from 220 1 to 5.5:1, in an amount of 9.0-28.0 mass %; the balance being water for injection.

12. A medicinal preparation of any one of claims 4-7 in dosage form adapted for oral use.

13. A medicinal preparation of any one of claims 4-7 in a single dosage form providing from 0.5 to 20 mg of said medicinal preparation per kg of body weight, calculated based on 9-oxoacridine-10-ylacetate or its residue.

14. A medicinal preparation of any one of claims 4 to 7 in dosage form suitable for topical application.

15. A method for treatment of diseases and/or conditions associated with or accompanied by immunologic status alteration, comprising administering a compound selected from the group consisting of:

a) one or more salts of 1-alkylamino-1-deoxypolyol and 9-oxoacridine-10-acetic acid of the general formula (I):

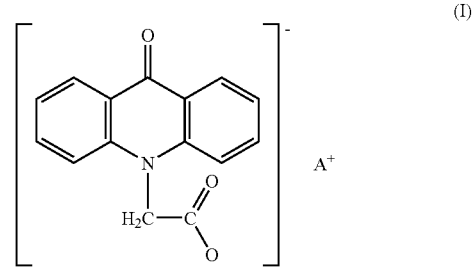

(I)

wherein $A^+$ is (II)

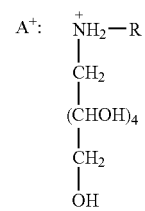

(II)

and R is selected from the group consisting of: ethyl; propyl; and butyl;

b) a mixture of said salt of formula (I) and one or more 1-alkylamino-1-deoxypolyols of the general formula (II):

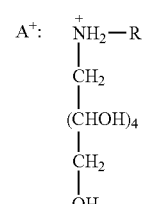
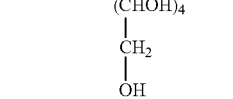

(II)

wherein R is selected from the group consisting of: ethyl; propyl; and butyl; and c) a mixture of 9-oxoacridine-10-acetic acid of the general formula (III):

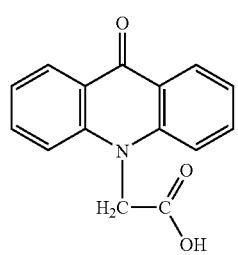

(III)

and one or more 1-alkylamino-1-deoxypolyol of the general formula (II):

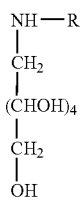

(II)

wherein R is selected from the group consisting of ethyl, propyl and butyl.

16. A method of prophylaxis and treatment according to claim 15, wherein the conditions are selected from the group consisting of HIV-infection; neuroinfection, meningitis, encephalitis; vital hepatitis A or B and/or C and/or D; herpes and/or cytomegalovirus infection; infectious mononucleosis; immunodeficiency, secondary immunodeficiency concerned with trauma, viral and/or bacterial and/or fungal infections and or parasitic invasions; parasitic invasions; bacterial infection, systemic rheumatic and connective tissue diseases, rheumatoid arthritis; degenerative inflammatory diseases of joints, secondary and primary osteoarthroses; prostatitis; oncologic diseases; pathological conditions caused by cytostatic therapy and/or exposure to radiation.

17. A method of treatment of said diseases and/or conditions according to claim 16, wherein said compound is administered once a day.

18. A method of prophylaxis and treatment of said diseases and/or conditions according to claim 17, wherein said medicinal preparation is administered in dose form 3 to 10 mg/kg, calculated as 9-oxoacridine-10-ylacetate or its residue.

19. A method of prophylaxis and treatment of said diseases and/or conditions according to claim 16, wherein said compound is administered parenterally as a course of treatment of from 5 to 12 introductions at days 1, 2, 4, 6, 8, 11, 14, 17, 20, 23, 26, 29.

20. A method of treatment of said diseases and/or conditions of humans according to claim 17, wherein said courses of treatment are repeated.

21. A method of treatment of said diseases and/or conditions according to claim 20, wherein said courses of treatment are repeated with an interval from 10 to 14 days.

22. A method of prophylaxis and treatment of said diseases and/or conditions according to claim 20, wherein said courses of treatment are repeated no less than twice.

23. A method of prophylaxis and treatment of said diseases and/or conditions according to claim 16, wherein compound is used as a monotherapeutic agent and also as a constituent of complex and/or combined therapy.

* * * * *